(12) United States Patent
Shao et al.

(10) Patent No.: US 10,197,697 B2
(45) Date of Patent: Feb. 5, 2019

(54) MODELING SUBTERRANEAN FORMATION PERMEABILITY

(71) Applicant: Halliburton Energy Services, Inc., Houston, TX (US)

(72) Inventors: Wei Shao, Conroe, TX (US); Songhua Chen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 316 days.

(21) Appl. No.: 14/397,835

(22) PCT Filed: Dec. 12, 2013

(86) PCT No.: PCT/US2013/074804
§ 371 (c)(1),
(2) Date: Oct. 29, 2014

(87) PCT Pub. No.: WO2015/088542
PCT Pub. Date: Jun. 18, 2015

(65) Prior Publication Data
US 2016/0231450 A1  Aug. 11, 2016

(51) Int. Cl.
*G01V 3/32* (2006.01)
*G01N 24/08* (2006.01)
*G01R 33/44* (2006.01)

(52) U.S. Cl.
CPC ............ *G01V 3/32* (2013.01); *G01N 24/081* (2013.01); *G01R 33/448* (2013.01)

(58) Field of Classification Search
CPC ........ G01N 24/081; G01N 21/55; G01V 3/32; G01R 33/5617
See application file for complete search history.

(56) References Cited

U.S. PATENT DOCUMENTS

| | | |
|---|---|---|
| 5,517,115 A | 5/1996 | Prammer |
| 7,091,719 B2 | 8/2006 | Freedman |

(Continued)

FOREIGN PATENT DOCUMENTS

| | | |
|---|---|---|
| EP | 1003053 | 5/2000 |
| WO | 2013023299 | 2/2013 |

OTHER PUBLICATIONS

International Search Report and Written Opinion of the International Searching Authority issued in International Application No. PCT/US2013/074804 dated Sep. 12, 2014; 10 pages.

(Continued)

*Primary Examiner* — Kyle R Quigley
(74) *Attorney, Agent, or Firm* — Benjamin Fite; Parker Justiss, P.C.

(57) ABSTRACT

Systems, methods, and software for modeling subterranean formation permeability are described. In some aspects, a method of training a subterranean formation permeability model based on NMR data includes accessing relaxation-time distributions generated from NMR measurements associated with a subterranean region. Multiple sets of principal components are generated from the relaxation-time distributions. Each set of principal components represents a respective one of the relaxation-time distributions. Parameters for weighted radial basis functions are computed based on the sets of principal components. A subterranean formation permeability model that includes the weighted radial basis functions and the computed parameters is produced.

25 Claims, 20 Drawing Sheets

(56) References Cited

U.S. PATENT DOCUMENTS

| | | | |
|---|---|---|---|
| 7,309,983 | B2 | 12/2007 | Freedman |
| 8,195,399 | B2 | 6/2012 | Gladkikh et al. |
| 2002/0146160 | A1* | 10/2002 | Parker .................. A61B 5/7264 382/131 |
| 2003/0016013 | A1 | 1/2003 | Kruspe |
| 2003/0107374 | A1 | 6/2003 | Chen et al. |
| 2005/0242807 | A1 | 11/2005 | Freedman |
| 2006/0055403 | A1 | 3/2006 | Freedman |
| 2008/0036457 | A1 | 2/2008 | Thern et al. |
| 2008/0154509 | A1 | 6/2008 | Heaton |
| 2008/0183390 | A1 | 7/2008 | Hamdan et al. |
| 2008/0206887 | A1 | 8/2008 | Chen et al. |
| 2009/0125239 | A1* | 5/2009 | Niemeyer ............ G01N 24/081 702/11 |
| 2009/0174402 | A1 | 7/2009 | Rottengatter et al. |
| 2009/0292473 | A1 | 11/2009 | Kruspe et al. |
| 2010/0138157 | A1 | 6/2010 | Sun et al. |
| 2010/0271019 | A1 | 10/2010 | Anand |
| 2011/0025324 | A1 | 2/2011 | Fransson et al. |
| 2012/0065888 | A1* | 3/2012 | Wu ......................... G01V 3/32 702/8 |

OTHER PUBLICATIONS

International Search Report and Written Opinion of the International Searching Authority issued in International Application No. PCT/US2013/074810 dated Sep. 12, 2014; 10 pages.

Abragam, "Principles of Nuclear Magnetism," ISBN-10: 019852014X, ISBN-13, 978-0198520146 (p. 300) 3 pages.

Anand et al, "Predicting Effective Permeability to Oil in Sandstone and Carbonate Reservoirs from Well Logging Data.", SPE 134011, Sep. 19-22, 2010, 19 pages.

Bloembergen et al., "Relaxation Effects in Nuclear Magnetic Resonance Absorption" Physical Review, Apr. 1, 1948, vol. 73, No. 7, pp. 679-712.

Bryan et al., "In-Situ Viscosity of Oil Sands Using Low-Field NMR", J. Can. Petro. Tech., vol. 44(9), Sep. 2005, pp. 23-29.

Bryan et al., "Oil-Viscosity Predictions from Low-Field NMR Measurements", SPE Reservoir Evaluation & Engineering, Feb. 2005, pp. 44-52.

Chen et al, "A New NMR $T_1$ Measurement Technique for Gas Shale, Heavy Oil, and Microporosity Characterizations," International Symposium of the Society of Core Analysts, Aug. 2012, 12 pages.

Chen et al., "Value of NMR Logging for Heavy Oil Characterization", World Heavy Oil Congress Paper 2008-353, Mar. 12, 2008, 16 pages.

Cheng et al., "Power-law Relationship between the Viscosity of Heavy Oils and NMR Relaxation", SPWLA 50th Annual Logging Symposium, Jun. 21-24, 2009, 7 pages.

Coates et al., "The MRIL* in Conoco 33-1, An Investigation of a New Magnetic Resonance Imaging Log", SPWLA 32nd Annual Logging Symposium, Jun. 16-19, 1991, 24 pages.

Gao et al, "New Method for Predicting Capillary Pressure Curves from NMR Data in Carbonate Rocks", SPWLA 52nd Annual Logging Symposium, May 14-18, 2011, 11 pages.

Kenyon et al, "A Three-Part Study of NMR Longitudinal Relaxation Properties of Water-Saturated Sandstones", SPE Formation Evaluation, Sep. 1988, 622-636.

Kleinberg et al., "NMR Properties of Reservoir Fluids", The Log Analyst, Nov.-Dec. 1996, pp. 20-32.

Kozeny, "Kozeny-Carman Equation", Wikipedia, last modified Apr. 20, 2013, 2 pages, retrieved from Internet at http://en.wikipedia.org/w/index.php?title=Kozeny-Carman_equation&oldid=551352710.

La Torraca et al., Low-Field NMR Determinations of the Properties of Heavy Oils and Water-in-Oil Emulsions; Magn. Reson. Img., vol. 16, No. 5-6, Published in 1998, pp. 659-662.

Orr, "Introduction to Radial Basis Function Networks," Apr. 1996, 67 pages.

Morriss et al., Hydrocarbon Saturation and Viscosity Estimation from NMR Logging in the Belridge Diatomite, SPWLA 35th Annual Logging Symposium, Jun. 19-22, 1994, 24 pages.

Nicot et al., "Improvement of Viscosity Prediction Using NMR Relaxation", SPWLA 48th Annual Logging Symposium, Jun. 3-6, 2007, 7 pages.

Orr, "Matlab Functions for Radial Basis Function Networks", Institute for Adaptive and Neural Computation Division of Informatics, Jul. 9, 1999, 69 pages.

Shafer et al, "Methods and Procedures for Calibrating NMR Log Derived Permeabilities," 11th Formation Evaluation Symposium of Japan, Oct. 5-6, 2005, 15 pages.

Worthington, "The Effect of Scale on the Petrophysical Estimation of Intergranular Permeability", Petrophysics, vol. 45, No. 1, Jan.-Feb. 2004, pp. 59-72.

Zhang et al., "Some Exceptions to Default NMR Rock and Fluid Properties", SPWLA 39th Annual Logging Symposium, May 26-29, 1998, 14 pages.

"Principal Component Analysis", Wikipedia, last modified Sep. 28, 2013, 19 pages, retrieved from internet at: http://en.wikipedia.org/wiki/Principal_component_analysis.

Chen et al., "Modeling Subterranean Fluid Viscosity," PCT International Application No. PCT/US2013/074810, filed Dec. 12, 2013, 52 pages.

Anand et al, "New methods for predicting properties of live oils from NMR," SPWLA 50th annual logging symposium, Jun. 24, 2009, <https://www.onepetro.org/download/conference-paper/SPWLA-2009-88680?id=conference-paper/SPWLA-2009-88680>.

Trevizan, W., et al., "Method for Predicting Permeability of Complex Carbonate Reservoirs Using NMR Logging Measurements," Petrophysics, vol. 55, No. 3, Jun. 2014, pp. 240-252.

Anand, V., et al., "Predicting Effective Permeability to Oil in Sandstone and Carbonate Reservoirs from Well-Logging Data," SPE Reservoir Evaluation & Engineering, Dec. 2011, pp. 750-762.

* cited by examiner

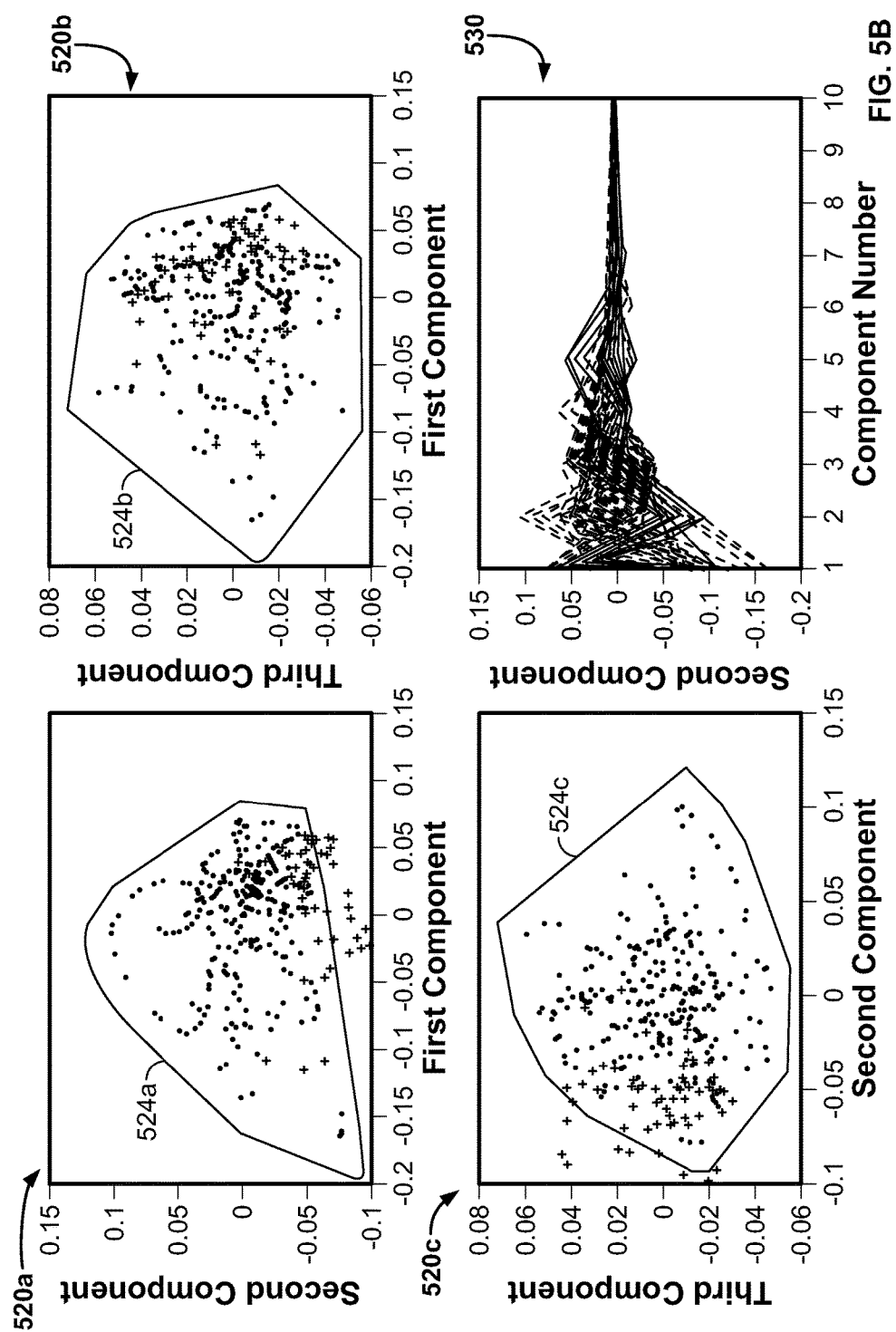

MODELING SUBTERRANEAN FORMATION PERMEABILITY

CLAIM OF PRIORITY

This application is a U.S. National Stage of International Application No. PCT/US2013/074804, filed Dec. 12, 2013.

BACKGROUND

This specification relates to modeling subterranean formation permeability based on nuclear magnetic resonance (NMR) data associated with a subterranean region.

In the field of logging (e.g. wireline logging, logging while drilling (LWD) and measurement while drilling (MWD)), nuclear magnetic resonance (NMR) tools have been used to explore the subsurface based on the magnetic interactions with subsurface material. Some downhole NMR tools include a magnet assembly that produces a static magnetic field, and a coil assembly that generates radio frequency (RF) control signals and detects magnetic resonance phenomena in the subsurface material. Properties of the subsurface material can be identified from the detected phenomena.

DESCRIPTION OF DRAWINGS

FIGS. 5B and 5C include plots of principal components from two example wells.

DETAILED DESCRIPTION

Figure 1A:
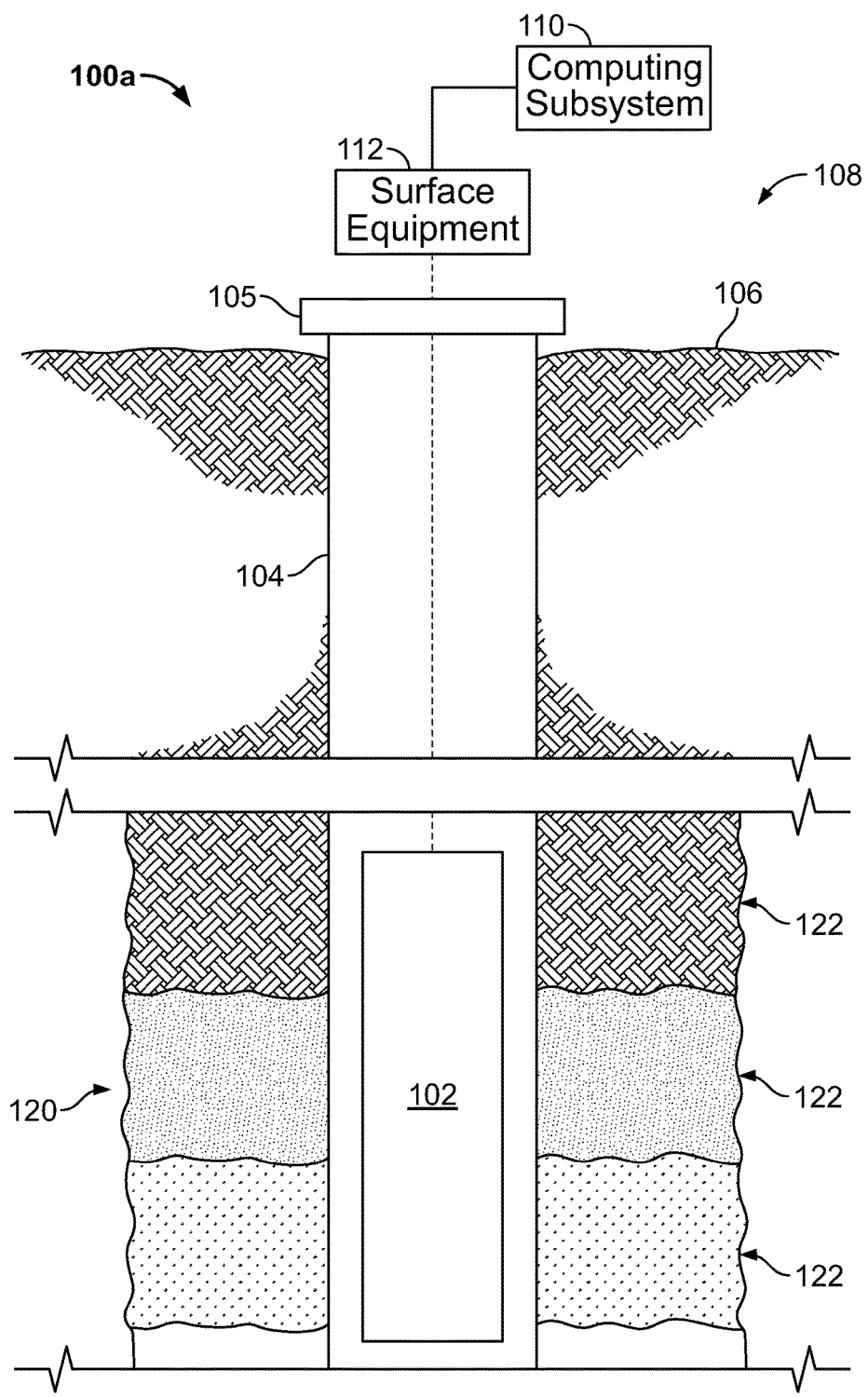
FIG. 1A is a diagram of an example well system.

FIG. 1A is a diagram of an example well system 100a. The example well system 100a includes an NMR logging system 108 and a subterranean region 120 beneath the ground surface 106. A well system can include additional or different features that are not shown in FIG. 1A. For example, the well system 100a may include additional drilling system components, wireline logging system components, etc.

The subterranean region 120 can include all or part of one or more subterranean formations or zones. The example subterranean region 120 shown in FIG. 1A includes multiple subsurface layers 122 and a wellbore 104 penetrated through the subsurface layers 122. The subsurface layers 122 can include sedimentary layers, rock layers, sand layers, or combinations of these and other types of subsurface layers. One or more of the subsurface layers can contain fluids, such as brine, oil, gas, etc. Although the example wellbore 104 shown in FIG. 1A is a vertical wellbore, the NMR logging system 108 can be implemented in other wellbore orientations. For example, the NMR logging system 108 may be adapted for horizontal wellbores, slant wellbores, curved wellbores, vertical wellbores, or combinations of these.

The example NMR logging system 108 includes a logging tool 102, surface equipment 112, and a computing subsystem 110. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. An NMR logging system can include additional or different features, and the features of an NMR logging system can be arranged and operated as represented in FIG. 1A or in another manner.

In some instances, all or part of the computing subsystem 110 can be implemented as a component of, or can be integrated with one or more components of, the surface equipment 112, the logging tool 102 or both. In some cases, the computing subsystem 110 can be implemented as one or more computing structures separate from the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The well system 100a can include communication or telemetry equipment that allow communication among the computing subsystem 110, the logging tool 102, and other components of the NMR logging system 108. For example, the components of the NMR logging system 108 can each include one or more transceivers or similar apparatus for wired or wireless data communication among the various components. For example, the NMR logging system 108 can include systems and apparatus for wireline telemetry, wired pipe telemetry, mud pulse telemetry, acoustic telemetry, electromagnetic telemetry, or a combination of these and other types of telemetry. In some cases, the logging tool 102 receives commands, status signals, or other types of information from the computing subsystem 110 or another source. In some cases, the computing subsystem 110 receives logging data, status signals, or other types of information from the logging tool 102 or another source.

NMR logging operations can be performed in connection with various types of downhole operations at various stages in the lifetime of a well system. Structural attributes and components of the surface equipment 112 and logging tool 102 can be adapted for various types of NMR logging operations. For example, NMR logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

Figure 1B:
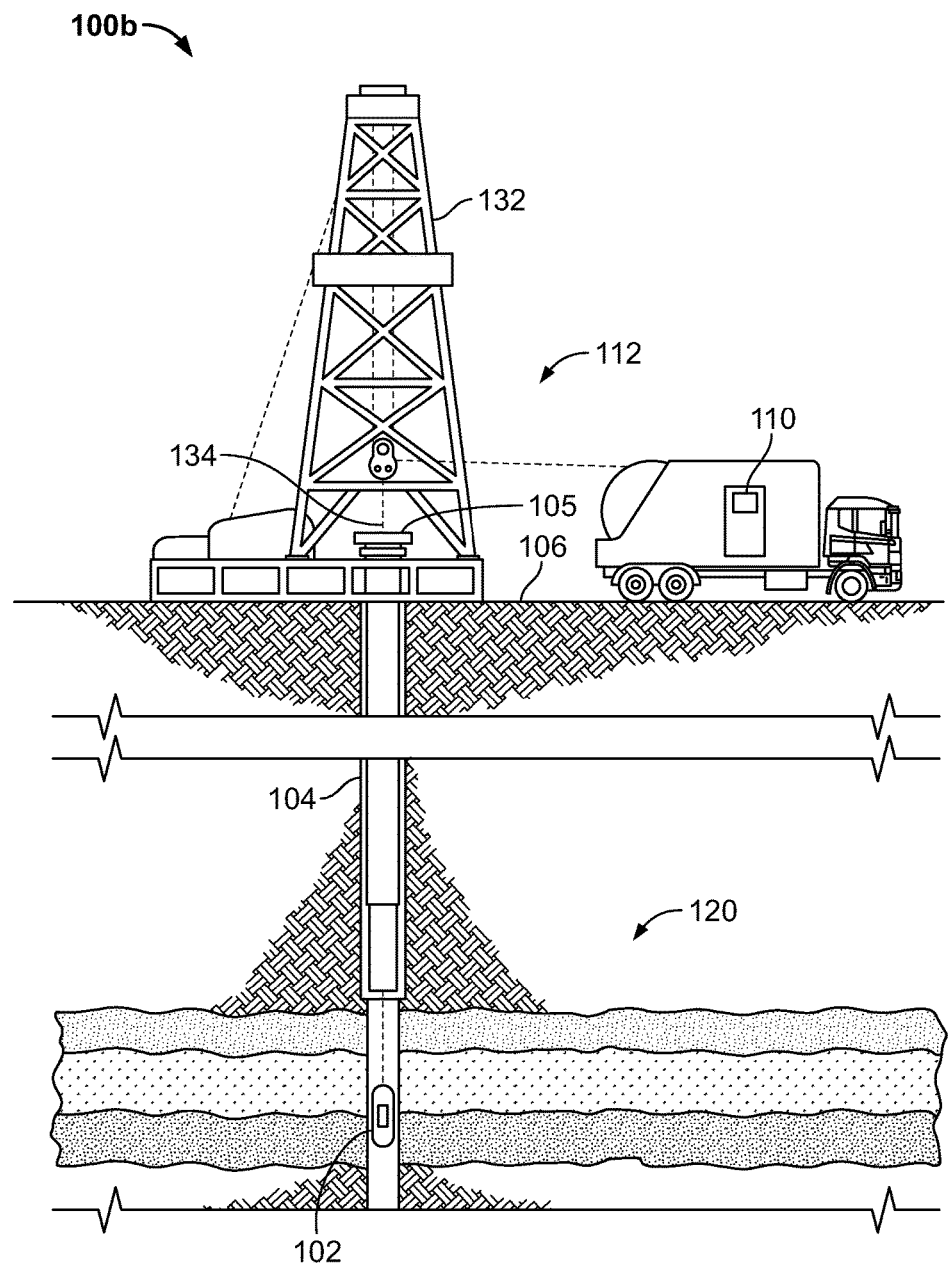
FIG. 1B is a diagram of an example well system that includes an NMR logging tool in a wireline logging environment.

In some examples, NMR logging operations are performed during wireline logging operations. FIG. 1B shows an example well system 100b that includes the NMR logging tool 102 in a wireline logging environment. In some example wireline logging operations, the surface equipment 112 includes a platform above the surface 106 equipped with a derrick 132 that supports a wireline cable 134 that extends into the wellbore 104. Wireline logging operations can be performed, for example, after a drill string is removed from the wellbore 104, to allow the wireline logging tool 102 to be lowered by wireline or logging cable into the wellbore 104.

Figure 1C:
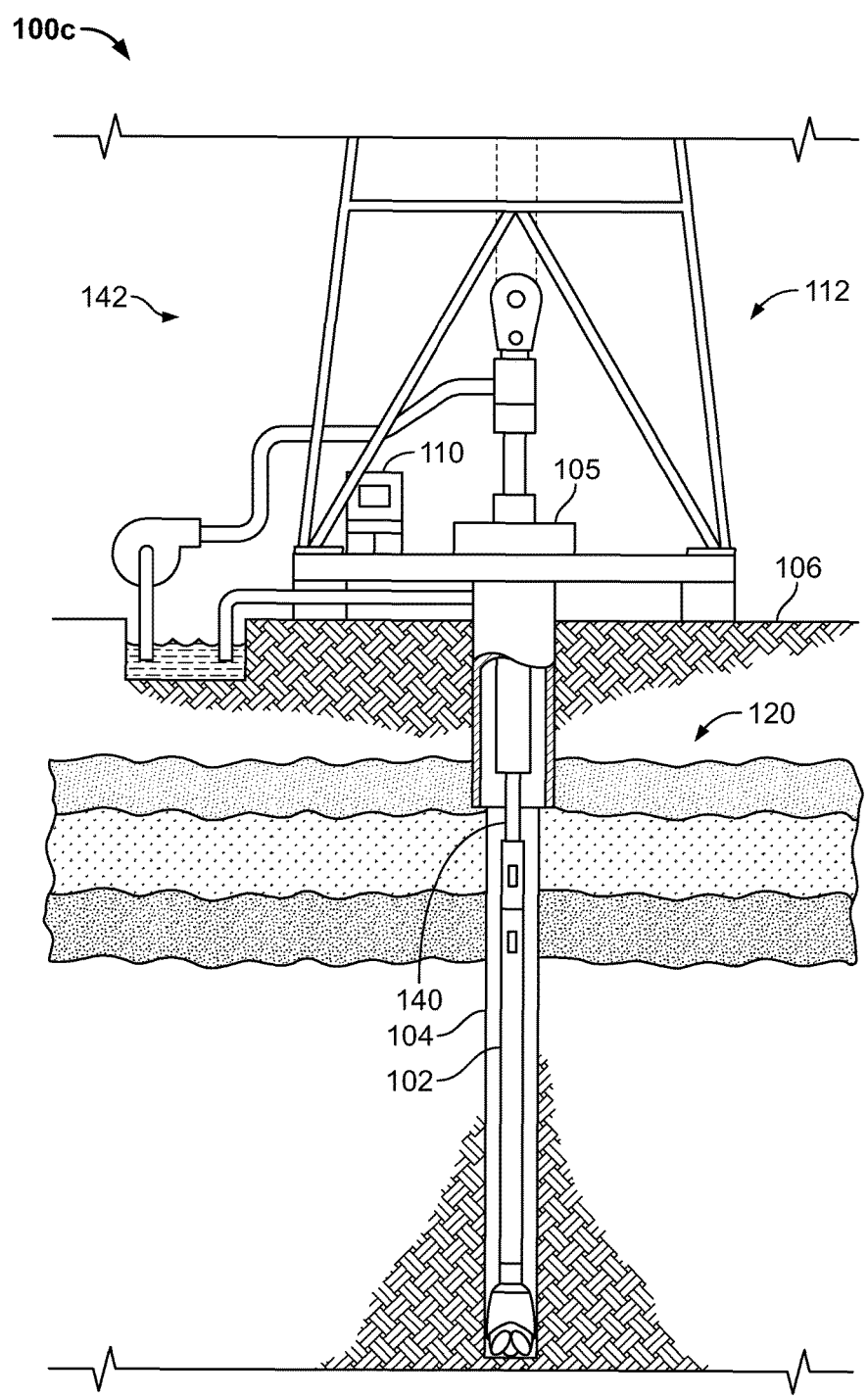
FIG. 1C is a diagram of an example well system that includes an NMR logging tool in a logging while drilling (LWD) environment.

In some examples, NMR logging operations are performed during drilling operations. FIG. 1C shows an example well system 100c that includes the NMR logging tool 102 in a logging while drilling (LWD) environment. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill a wellbore penetrating the subterranean region 120. The drill string 140 may include, for example, a kelly, drill pipe, a bottom hole assembly, and other components. The bottom hole assembly on the drill string may include drill collars, drill bits, the logging tool 102, and other components. The logging tools may include measuring while drilling (MWD) tools, LWD tools, and others.

In some example implementations, the logging tool 102 includes an NMR tool for obtaining NMR measurements from the subterranean region 120. As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest. In some example implementations, the logging tool 102 collects data while the drill string 140 is moving, for example, while it is being tripped in or tripped out of the wellbore 104.

In some example implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, material content, or other properties of the subsurface layers 122 based on the NMR measurements acquired by the logging tool 102 in the wellbore 104.

In some implementations, the logging tool 102 obtains NMR signals by polarizing nuclear spins in the formation 120 and pulsing the nuclei with a radio frequency (RF) magnetic field. Various pulse sequences (i.e., series of radio frequency pulses, delays, and other operations) can be used to obtain NMR signals, including the Can Purcell Meiboom Gill (CPMG) sequence (in which the spins are first tipped using a tipping pulse followed by a series of refocusing pulses), the Optimized Refocusing Pulse Sequence (ORPS) in which the refocusing pulses are less than 180°, a saturation recovery pulse sequence, and other pulse sequences.

The acquired spin-echo signals (or other NMR data) may be processed (e.g., inverted, transformed, etc.) to a relaxation-time distribution (e.g., a distribution of a transverse relaxation times $T_2$ or a distribution of longitudinal relaxation times $T_1$), or both. The relaxation-time distribution can be used to determine various physical properties of the formation by solving one or more inverse problems. In some cases, relaxation-time distributions are acquired for multiple logging points and used to train a model of the subterranean region. In some cases, relaxation-time distributions are acquired for multiple logging points and used to predict properties of the subterranean region.

Figure 2:
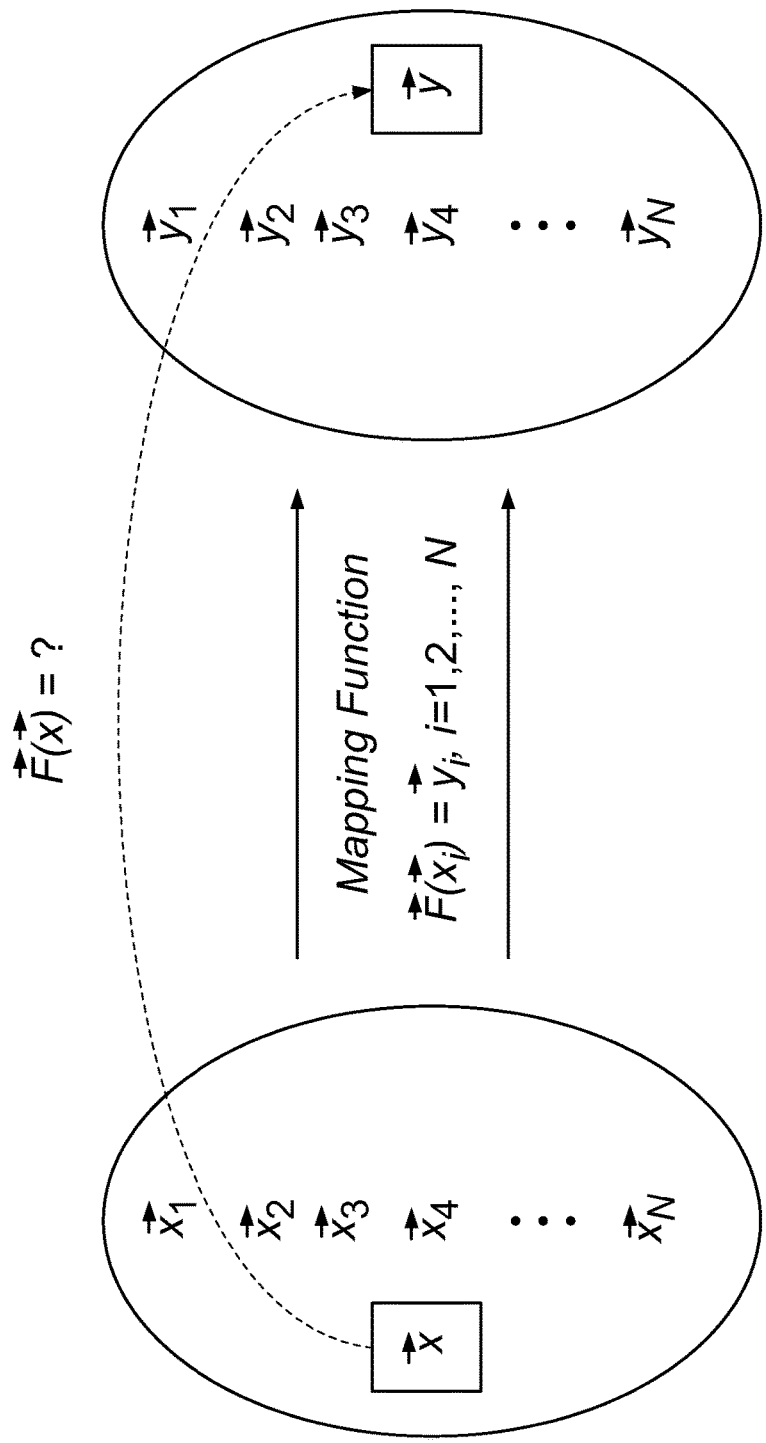
FIG. 2 is a diagram of an example mapping function.

Inverse problems encountered in well logging and geophysical applications may involve predicting the physical properties of some underlying system given a set of measurements (e.g., a set of relaxation-time distributions). Referring to FIG. 2, consider a database having a set of distinct input data $\vec{x}_i \in R^n$ (i.e., the inputs are n-dimensional vectors) and a set of corresponding outputs, $\vec{y}_i \in R^m$, for i=1, ..., N, where N is the number of cases in the database. The different cases in the database represent different states of the underlying physical system. In this notation, $\vec{y}_i$ values represent samples of the function that one wants to approximate (e.g., by a model), and $\vec{x}_i$ values are the distinct points at which the function is given. The database is used to construct a mapping function such that, given measurements $\vec{x}$ that are not in the database, one can predict the properties $F(\vec{x})$ of the physical system that is consistent with the measurements. The mapping function can solve the inverse problem of predicting the physical properties of the system from the measurements.

Mapping functions can be used to solve the inverse problem of predicting the permeability of a subterranean formation based on measurements obtained using NMR. In some cases, mapping can be used to develop a correlation that links core permeability measurements with in-situ NMR logging measurements. In some cases, the use of a direct correlation can bypass the complexity of indirect correlations (e.g., different fluid saturation and wettability states) between laboratory NMR and logging data. In some cases, Radial Basis Functions (RBFs) can be used to construct a subterranean formation permeability model, and Principal Component Analysis (PCA) can be used to preprocess the data in the training database.

Figure 3:
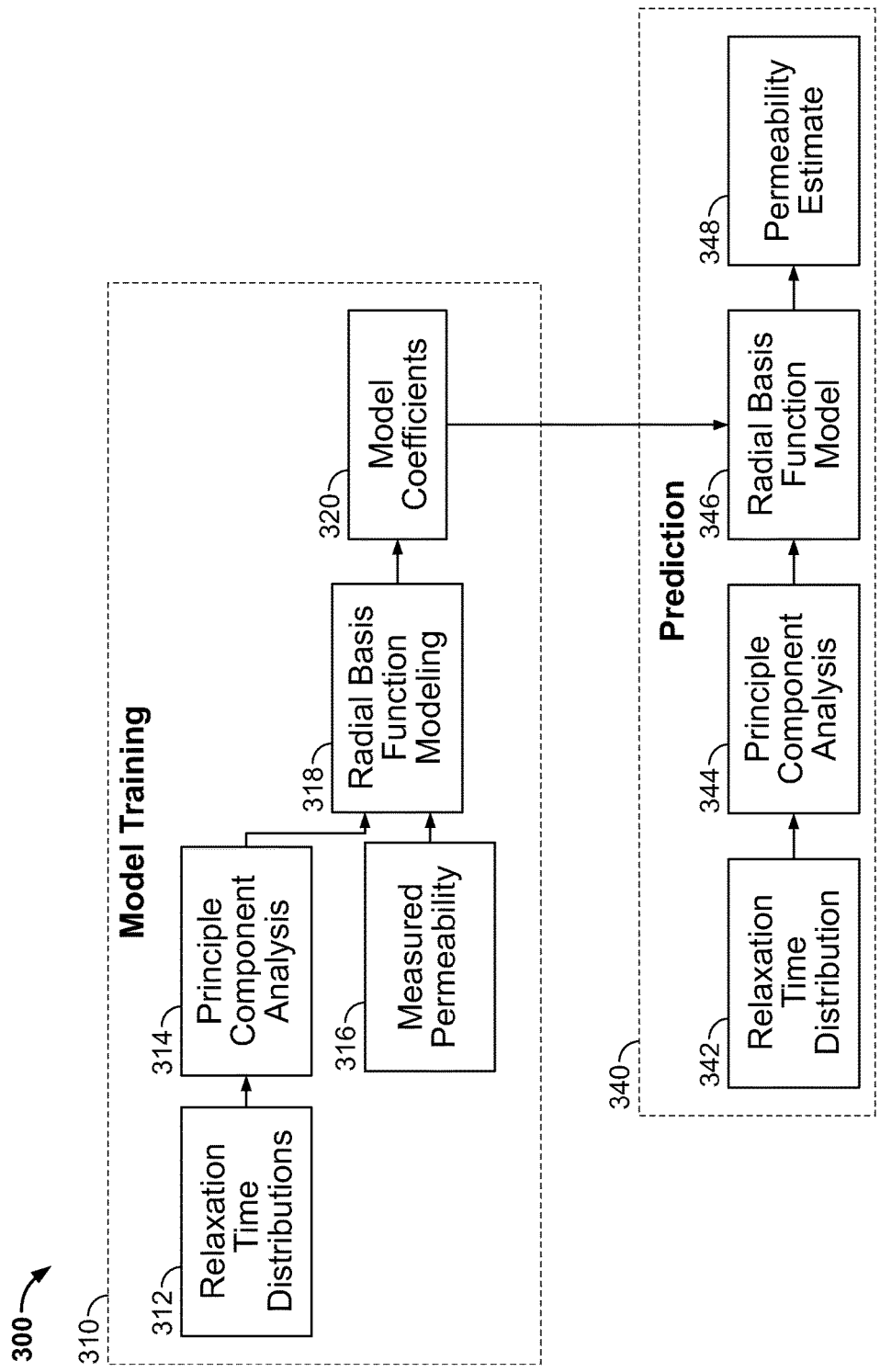
FIG. 3 is a diagram of an example process for modeling the permeability of a subterranean formation.

An example process 300 for predicting the permeability of a subterranean formation from NMR measurements is shown in FIG. 3. The example process 300 shown in FIG. 3 includes a model training sub-process 310 and permeability prediction sub-process 340. The model training sub-process 310 can be used to develop a mapping function based on a database of NMR and permeability measurements; the permeability prediction sub-process 340 can be used to predict permeability based on one or more NMR measurements and the developed mapping function. The process 300 can include additional or different sub-processes or other operations, and the operations can be configured as shown or in another manner.

The example model training sub-process 310 includes generating a training database of relaxation distributions obtained from NMR logging of one or more subterranean formations (312). The training database of relaxation distributions can be reduced to a subset of key components (i.e., the "principal" components of the database) through principal component analysis (314). Measured permeability values are obtained for the NMR-logged subterranean formations (316). The principal components of the training database and the measured permeability values can be used to train the RBF model (318). Training the RBF model generates model coefficients (320); the resulting RBF model and its coefficients can be used as a mapping function that predicts the permeability of a subterranean formation based on input relaxation-time distributions.

In some implementations, the permeability prediction sub-process 340 includes obtaining an input relaxation-time distribution from NMR logging of a subterranean formation (342), and converting the relaxation distribution to the same subset of principal components identified during model training (344). The principal components of the input relaxation-time distribution can then be used as an input in the RBF model, using the modeling coefficients identified during model training (346), resulting in a permeability estimate (348).

In some examples, NMR signals are obtained in situ (e.g., by using NMR logging tools to obtain measurements of formations under the earth's surface). In some examples, NMR signals can be obtained ex situ (e.g., by using NMR logging tools to obtain measurements of core samples that have been removed from the earth's surface). The NMR signals (obtained in situ or ex situ) can be converted into relaxation-time distributions. In some implementations, each NMR signal is a spin-echo train that includes a series of multi-exponential decays, and the relaxation-time distribution can be a histogram of the decay rates extracted from the spin-echo train.

In some examples, an NMR signal can be described as multiple components resulting from multiple different relaxation times in the measured region. For example, the signal amplitude of the first echo may be expressed approximately by:

$$\phi(t = TE) = \sum_{i=1}^{N} \phi_i(TE),$$

where $$\phi_i(t) = c_i \exp\left(-\frac{t}{T_{2i}}\right).$$

Here, each of the N components has a respective amplitude of $\phi_i$, an initial amplitude $c_i$, and a characteristic relaxation time $T_{2i}$. In some cases, some of the components (i<k) (those having the shortest relaxation times $T_{2i}$) decay too quickly to produce a measurable signal at the echo time, and the measurable signal amplitude is:

$$\sum_{i=k}^{N} \phi_i,$$

and the total signal is:

$$\sum_{i=k}^{N} \phi_i.$$

The $T_2$ distribution can then be described as:

$$\phi:\{\phi_i \text{ vs. } T_{2i}, \text{ where } i=1:N\}.$$

For data acquired with a finite TE, the apparent $T_2$ distribution can be described as:

$$\phi_{app}(TE:\{\phi_i \text{ vs. } T_{2i}, \text{ where } i=k:N \text{ and } \phi_i=0 \text{ for } i<k\}.$$

Typically, NMR measurements are affected by noise, and the noise is introduced into the relaxation-time distributions derived from the NMR measurements. In some instances, important structures of the relaxation-time distributions are less affected by the noise, and these important structures can be used for training the RBF model. In addition, data within each relaxation distribution are often highly correlated, and thus contain redundancies that can unnecessarily increase the complexity of the RBF model. To account for these phenomena, PCA (314) can be used to reduce each of the relaxation-time distributions to a subset of key components. In some cases, PCA provides a rank ordering of variances in the data. The rank ordering can be structured such that principal components with larger associated variances represent important structure (signal), while those with lower variances represent noise or insignificant information.

In some implementations, Principal Component Analysis (PCA) transforms a set of data vectors from an initial coordinate system to a new coordinate system. The new coordinate system can be defined such that when the data vectors are expressed in the new coordinate system all (or substantially all) significant variations among the data vectors are described by a reduced number of vector components. Thus, although the data vectors may have the same number of components in both coordinate systems, most of the vector components in the new coordinate system can be ignored or neglected; the retained vector components form a set of principal components that are used to analyze the data.

In some cases, the $k^{th}$ principal component is the $k^{th}$ component of a transformed data vector in the new coordinate system. The proportion of the total variance accounted for by $k^{th}$ principal component can be:

$$\frac{\lambda_k}{\sum_{i=1}^n \lambda_i},$$

where $\lambda_i$, i=1, . . . , n are the eigenvalues of the covariance matrix of the training data set. Each of the eigenvalues quantifies the variance of the corresponding principal component.

Figure 4:
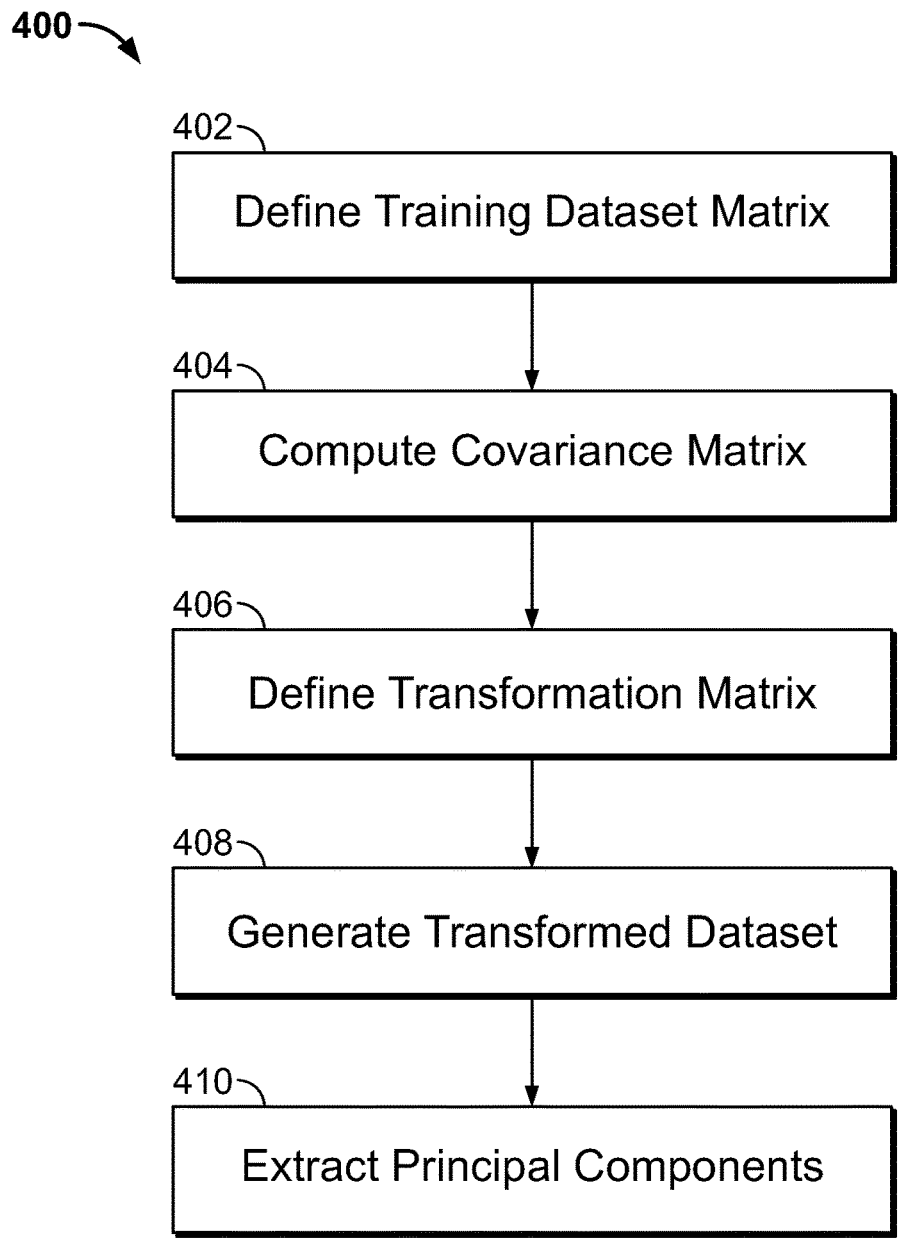
FIG. 4 is a diagram of an example principal component analysis process.

Referring to FIG. 4, an example principal component analysis process 400 can be used to generate sets of principal components from relaxation-time distributions, where each set of principal components represents a respective one of the relaxation-time distributions. The process 400 can include additional or different operations, and the operation can be performed in the order shown or in another order.

At 402, a dataset matrix X is formed from the relaxation-time distributions. Each of the n relaxation-time distributions has p elements, so the dataset matrix X can be an n×p matrix (n rows, p columns), in which each of the relaxation-time distributions forms a respective row. The training dataset of relaxation-time distributions can be represented in another manner, using any suitable data format, data structure, or data type.

The relaxation-time distributions can include distributions of transverse relaxation times or longitudinal relaxation times obtained from NMR data. In some cases, the area integration of each distribution is normalized to a common normalizing value. For example, the normalizing value can be 1 or another constant value. To normalize a distribution, the values in the distribution can be multiplied or scaled uniformly so that the area of the scaled distribution is equal to the normalizing value.

At 404, the eigenvectors of the covariance matrix C of dataset matrix X are determined. The covariance matrix C may be computed as $C=X^T X$, where $X^T$ is the transpose of the dataset matrix X, or the covariance matrix can be computed in another manner. In some instances, one or more of the eigenvectors can be obtained without explicitly computing the covariance matrix.

At 406, a transformation matrix $W_L$ is formed, where $W_L$ is a p×l matrix whose columns are eigenvectors of the covariance matrix C. The transformation matrix $W_L$ can be formed from the l eigenvectors that correspond to the l largest eigenvalues of the covariance matrix C. The eigenvectors and eigenvalues of the covariance matrix C can be determined, for example, by conventional techniques for computing matrix eigenvectors and eigenvalues.

At 408, the dataset matrix X is converted to a new coordinate system; the transformation generates a transformed matrix $T=XW_L$. At 410, sets of principal components are extracted from the transformed matrix T. In some implementations, the transformed matrix T is an n×l matrix, and the $i^{th}$ row contains a set of principal components corresponding to the $i^{th}$ relaxation-time distribution in the dataset matrix X. For example, the matrix element T(i, k) (the element at the $k^{th}$ column and $i^{th}$ row) can represent the $k^{th}$ principal components of the $i^{th}$ relaxation-time distribution.

In some implementations, the data vectors (in the initial coordinate system) can be the $T_2$ distributions of the database obtained from NMR measurements, and each data vector can have 27 or 54 components. In some cases, the relaxation-time bins are evenly spaced along the logarithmically-scaled axis; or the bins may be spaced in another manner. After the data vectors are transformed to the new coordinate system, the first three principal components (i.e., the first three components of the transformed data vectors) can be retained for use in training (or using) the permeability model (410); the other 24 (or 51) components can be disregarded because they primarily represent noise or redundancy.

Figure 5A:
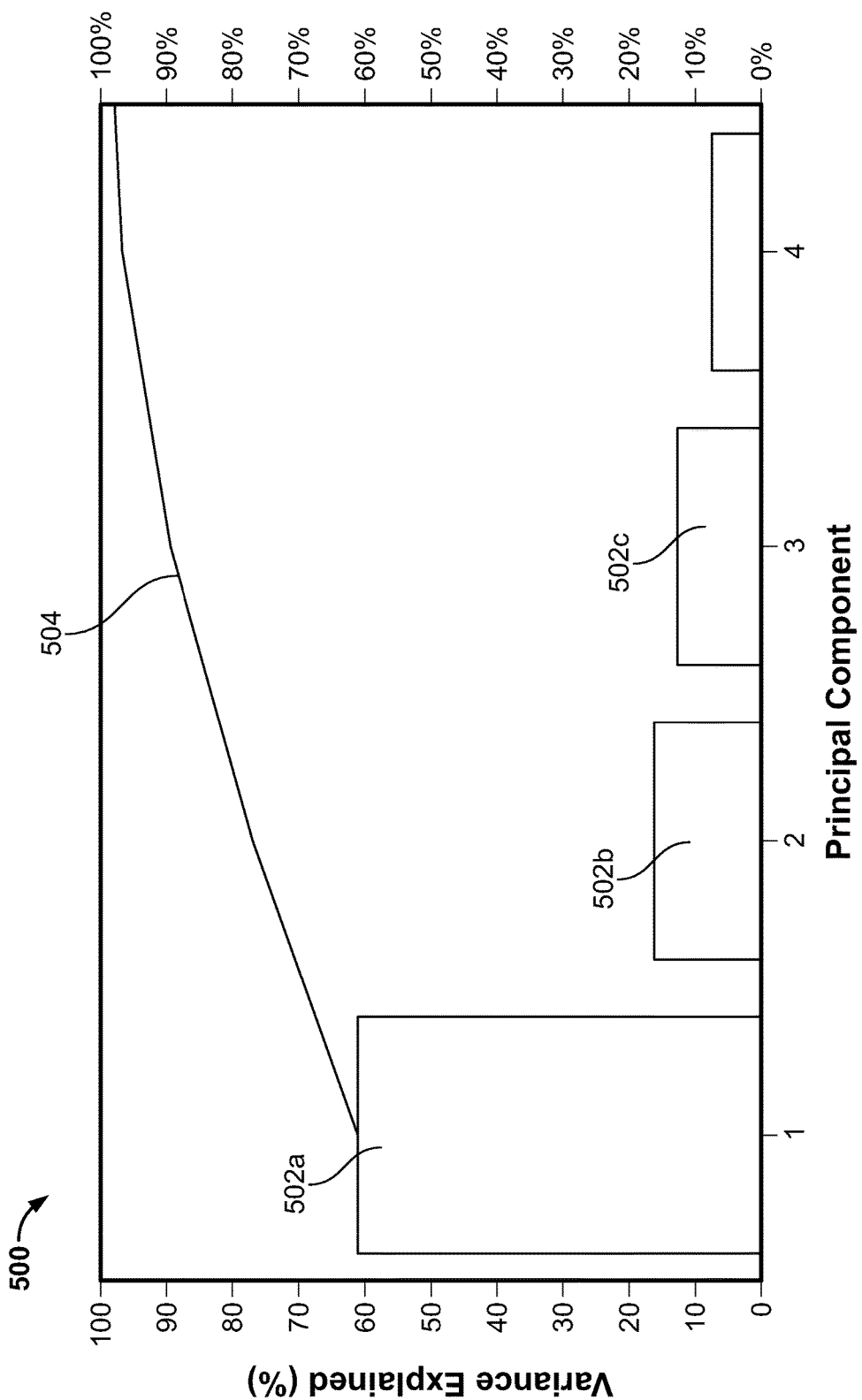
FIG. 5A is a plot that shows variance accounted for by individual principal components.

Referring to FIG. 5A, plot 500 shows that for an example database of $T_2$ distributions, the first three principal components 502a-c account for over 90% of the variances. In particular, the curve 504 in the plot 500 shows the cumulative variance after each additional principal component is added. With the understanding that lower variances represent noise or redundancy, the components having lower variances can be discarded. In some implementations, the number of retained components is determined by comparing the ratio:

$$\frac{\sum_{i=p+1}^n \lambda_i}{\sum_{i=1}^n \lambda_i}$$

with noise-to-signal ratio:

$$\frac{\sigma_{noise}^2}{\sigma_{signal}^2}$$

in the NMR measurement data, where p is the number of retained components. For example, in some implementations, NMR logging data is adequately stacked to reduce the noise to 1 pu. Assuming the average porosity is around 30 pu, the noise-to-signal ratio is about 3 percent. Thus, in this example, three principal components of the $T_2$ distribution should be retained. A greater number of principal components can be retained for use in training or using the permeability model. For example, in some implementations, four, five, six, or more principal components are retained.

Figure 5C:
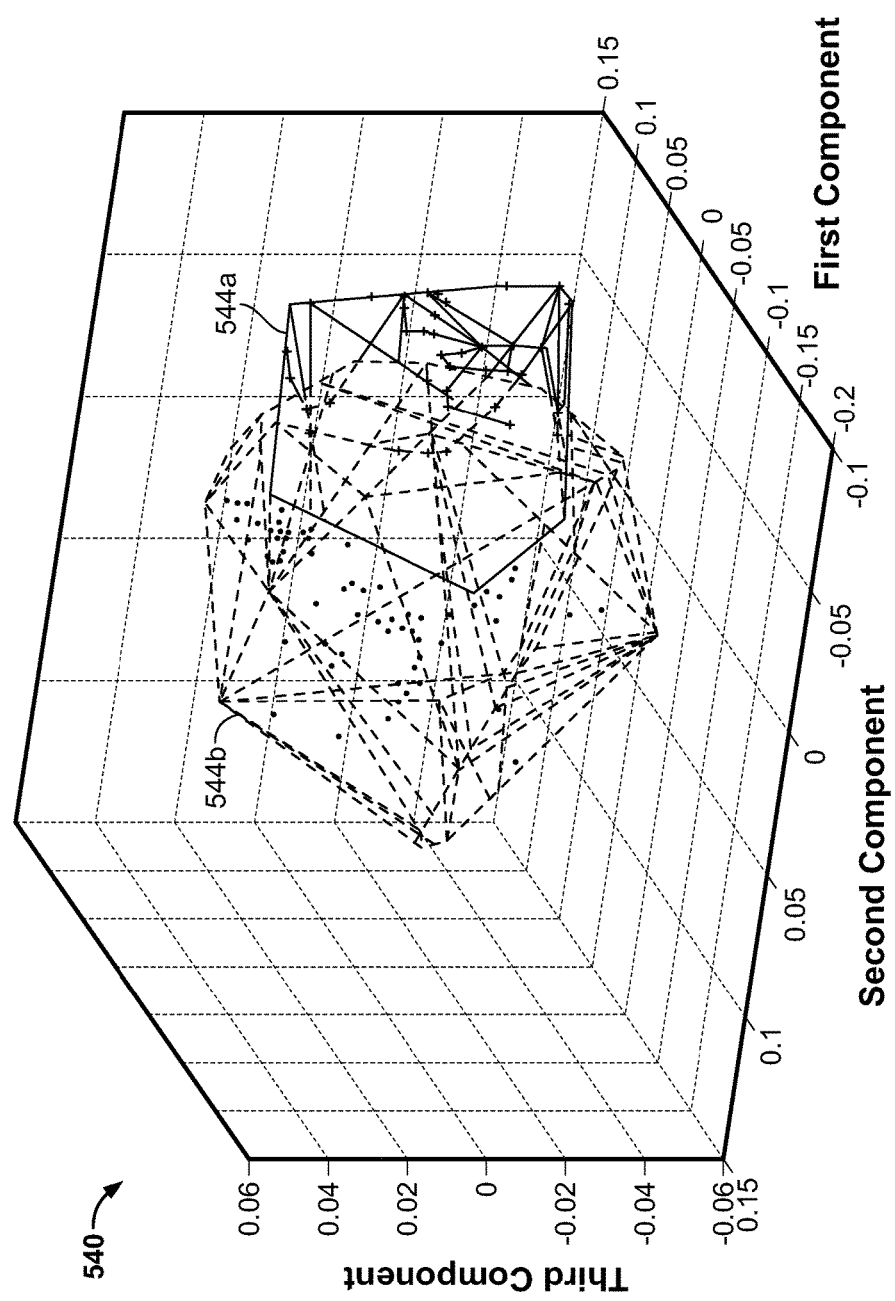

FIGS. 5B and 5C show data relating to an example principal component analysis of relaxation-time distributions from two wells. Data from well one (represented as circles in the plots 520a, 520b, 520c, and as dashed lines in the plots 530 and 540) are used as the training data set of an example RBF model. In this example, the input data are $T_2$ distributions, and the output data are permeability values. Data from well two (represented as crosses in the plots 520a, 520b, 520c, and as solid lines in the plots 530 and 540) are used for prediction. Principle component analysis is applied to the $T_2$ distributions of well one, and the $T_2$ distributions of well two are converted to a new coordinate system based on the principle component analysis of well one.

FIG. 5B shows three cross plots: the plot 520a of the first principal components versus the second principal components, the plot 520b of the first principal components versus the third principal components, and the plot 520c of the second principal components versus the third principal components. The polygons 524a, 524b, 524c enclose the components from well one in each plot. The RBF model is based on the training data points from well one (within the enclosed areas of the polygons 524a, 524b, 524c).

As shown in the cross plots 520a, 520b, 520c, most of the components from well two reside inside the polygons, but some reside outside the polygons. Predicted values (from well two) outside the polygons will be less reliable in some instances. The fourth plot 530 in FIG. 5B shows the values of the principle components from well one (dashed) and well two (solid) against the number (or index) of the principle components.

FIG. 5C shows a three-dimensional plot of the first three components from well one (dashed line) and well two (solid line). The space enclosed by the dashed polygon 544b represents the envelope of the RBF model, and the space enclosed by the solid polygon 544a contains the principle components from well two.

Permeability values can be obtained by laboratory core plug permeability measurements, production logging of subterranean formations (316 of FIG. 3), or other techniques. For the purposes of model training, these measured permeability values can be treated as "ground truth" values, and can be used to determine correlations between the measured NMR signals and corresponding formation permeability values. In some implementations, these permeability values can be obtained ex situ using any of a variety of permeability measurement instruments and techniques. For example, in some implementations, after a particular section of a subterranean region is logged using an NMR tool, core plug samples are removed from the subterranean region and measured in a laboratory setting.

The principal components of the training database and the measured permeability values can be used to train an RBF model, such as, for example, at 318 in FIG. 3. A radial basis function (RBF) is a function in the form of $\varphi(\|\vec{x}-\vec{x}_c\|)$, where $\|\vec{x}-\vec{x}_c\|$ is the Euclidean distance between the points $\vec{x}$ and $\vec{x}_c$, and where $\vec{x}$ is the variable and $\vec{x}_c$ is the center of the radial basis function. An RBF model $F(\vec{x})$ can be represented as a linear combination of radial basis functions. The RBF model can be used to approximate the physical system $f(\vec{x})$ to a certain degree of accuracy, for example, assuming the underlying physical system $f(\vec{x})$ is smooth and continuous.

The RBF model $F(\vec{x})$ can be derived by interpolating an input-output data set $\{(\vec{x}_i, \vec{y}_i)\}_{i=1}^N$ sampled from an underlying physical system $f(\vec{x})$, where $\{\vec{x}_i\}_{i=1}^N$ is the database of relaxation-time distributions transformed by PCA analysis, and $\{\vec{y}_i\}_{i=1}^N$ the measured permeability corresponding to each relaxation-time distribution. An RBF model can be represented $$F(\vec{x}_i) = \vec{y}_i, i=1,2,\ldots,N.$$

where, $$F(\vec{x}) = \sum_{i=1}^{N} \vec{w}_i \varphi(\|\vec{x}-\vec{c}_i\|).$$

In this example model, $$\{\vec{w}_i \varphi(\|\vec{x}-\vec{c}_i\|)\}_{i=1}^N$$

a set of weighted radial basis functions, N, $\vec{w}_i$, and $\vec{c}_i$ are model coefficients, and $$\{(\vec{x}_i, \vec{y}_i)\}_{i=1}^N$$

is the input-output training set.

In the above model, the parameters $$\{(\vec{c}_i)\}_{i=1}^N$$

represent the centers of the RBF model. In some implementations, the centers correspond to the inputted training parameters, which may include, for example, the database of relaxation-time distributions transformed by PCA analysis, principle components of the normalized relaxation-time distributions, the corresponding total porosities, or combinations of these and other input training parameters. In this case, the RBF model can be represented as:

$$F(\vec{x}) = \sum_{i=1}^{N} \vec{w}_i \varphi(\|\vec{x}-\vec{x}_i\|),$$

where N, $\vec{w}_i$, and $\vec{x}_i$ are the model coefficients. The function $\varphi$ can be a Gaussian function or another type of smooth function. For example, when the function $\varphi$ is a Gaussian, the matrix associated with the interpolation is well-conditioned, and the RBF inversion has a unique solution.

The coefficients of the RBF model can be determined by interpolation of the training datasets. In some instances, the coefficients $\vec{w}_i$ can be determined by requiring that the interpolation equations be satisfied exactly. For example, the coefficients can be a linear combination of the function values $$\vec{w}_i = \sum_{j=1}^{N} \Phi_{ij}^{-1} \vec{y}_j,$$

where $\Phi_{ij} = \varphi(\|\vec{x}_i - \vec{x}_j\|)$ is the N×N interpolation matrix The RBF model and model coefficients can be used to predict permeability based on an input relaxation-time distribution. An input relaxation-time distribution can be obtained from an input NMR signal, for example, using NMR signal inversion. In some implementations, this input NMR signal is obtained independently from the NMR signals used to train the model. For example, the input NMR signal is obtained from a subterranean formation with unknown permeability. The input NMR signal can be inverted into a relaxation-time distribution using an NMR inversion process similar to the NMR signal inversion described above.

The input relaxation-time distribution can then be remapped to the new coordinate system identified during model training. That is, the dataset matrix $X_{input}$, can be transformed to the new coordinate system by the operation $T_{input} = X_{input} W_L$, where the transformed matrix $T_{input}$ has l columns. Here, each element $T_{input}(i, k)$ (the element at the $k^{th}$ column, $i^{th}$ row) represents the $k^{th}$ principal component of the $i^{th}$ input relaxation-time distribution, and $W_L$ represents the transformation matrix identified during model training.

Transformed matrix $T_{input}$ can be input into the RBF model, using the model coefficients identified during model training. That is, if $T_{input}$ represents the vector elements of $\vec{x}$, the estimated permeability $F(\vec{x})$ can be determined by:

$$F(\vec{x}) = \sum_{i=1}^{N} \vec{w}_i \varphi(\|\vec{x} - \vec{c}_i\|),$$

where N, $\vec{w}_i$, and $\vec{c}_i$ are the model coefficients identified during model training. Thus, after model training, subsequent permeability estimates can be determined using independently acquired input NMR signals.

Figure 6:
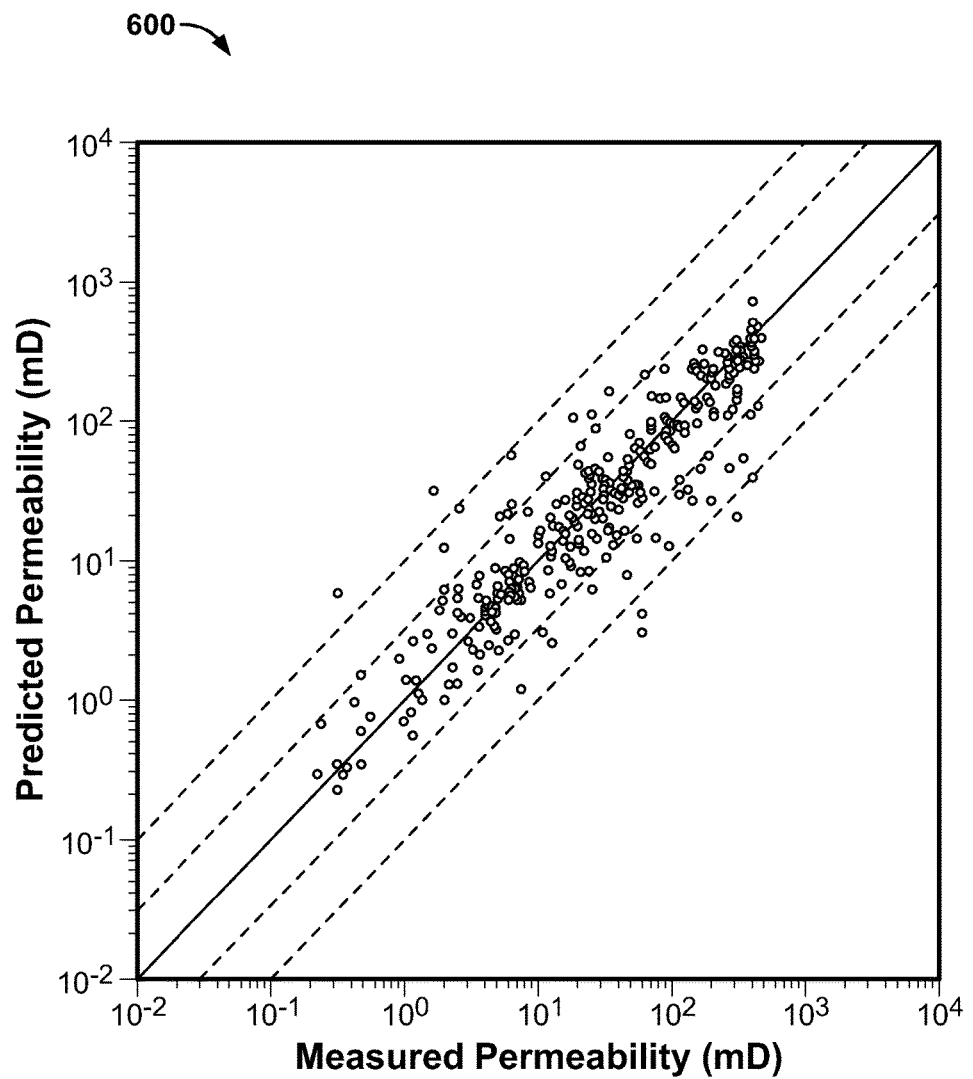
FIG. 6 is a plot that compares permeability predicted by an example model and measured permeability.

Referring to FIG. 6, the predicted permeability of the RBF model can be compared to the measured permeability using a "leave one out" method, in which a sample from the training data set is taken out and its permeability is predicted using the RBF model developed with the rest of the data in the training data set. Plot 600 shows that, using an example training database, the permeability predicted using the RBF model is generally well within one order of magnitude or less of the measured permeability.

In some implementations, using this technique, a single RBF model can be used for both lower permeability formations (e.g., formations having a permeability of approximately 1 milliDarcy (mD) or less and higher permeability formations (e.g., formations having a permeability of approximately 10 mD or greater). As such, in some implementations, no a priori knowledge about the formation's permeability is required in order to make a reliable permeability estimate.

Figure 7:
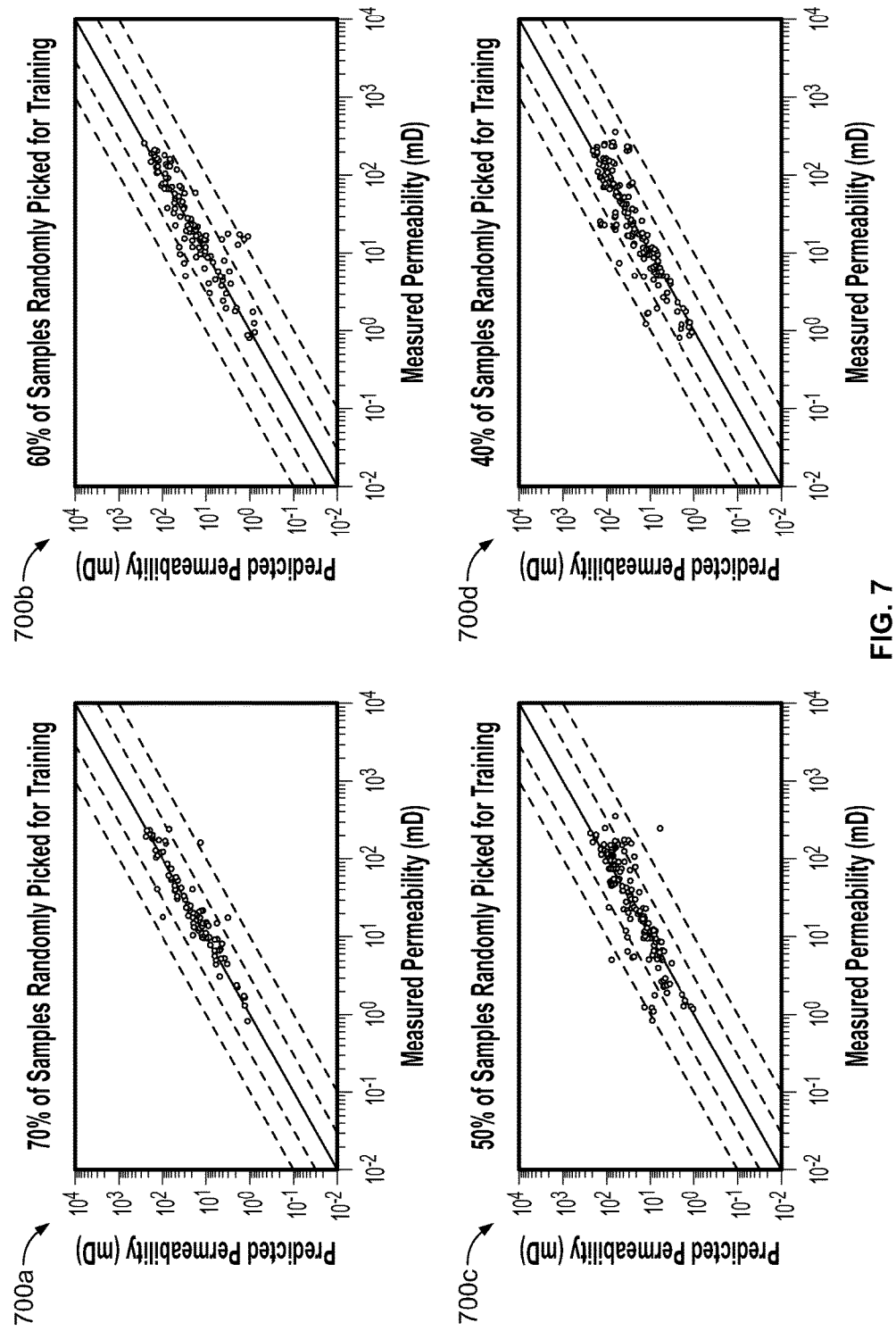
FIG. 7 includes plots that show the performance of an example RBF model when trained with varying numbers of training samples.

Though more training samples may improve the RBF model in some cases, using more samples as the centers in the RBF model does not necessarily result in better prediction performance in all cases. For instance, in some implementations, increasing the number of centers in an RBF model may result in an RBF model that over-fits the training database. Referring to FIG. 7, plots 700a-d show the performance of an RBF model trained with 70% randomly selected samples from an example database (plot 700a), an RBF model trained with 60% randomly selected samples from an example database (plot 700b), an RBF model trained with 50% randomly selected samples from an example database (plot 700c), and an RBF model trained with 40% randomly selected samples from an example database (plot 700d). Comparing plots 700c and 700d, the example RBF model trained with 40% randomly selected samples from the database performs better than the one trained with 50% randomly selected samples from the database. Hence, in some implementations, too many centers used for the RBF model may result in over-fitting, and ultimately, the performance of the RBF model may depend on the samples used for the centers. In some implementations, the number of samples used for the RBF centers can be selected empirically, or according to other selection criteria. In some cases, all the training samples are used during the training process, including some instances where forward selection is used to select the centers.

In some implementations, the relaxation-time distributions of the database and/or the input relaxation-time distribution can be normalized to a common normalizing value. For instance, in some implementations, the relaxation-time distributions can be separated into two parts: the relative shape of the distributions and the summation of the amplitudes of the distributions (i.e., the total porosities). Principle component analysis can be applied to the relative shape of the distributions. In some cases, the resulting RBF model and predictions are dependent on the relative shape of the distributions and the summation of the amplitudes of the distributions. In some implementations, the relaxation-time distributions can be normalized to a common normalizing value of one (i.e., normalized such that each relaxation-time distribution has a unit integral). In some implementations, the relaxation-time distribution can be normalized to other common normalizing values (e.g., 0.5, 1.5, 2, 2.5, and so forth).

The RBF model described above is an interpolation method, and its performance may depend on the quality of the training database. For example, if the permeability measurements of the training database are very noisy and/or if too many centers are used for the interpolation, the RBF model can become overly sensitive to the details of the data, which may result in oscillatory behavior due to over-fitting. These detrimental effects can be mitigated in various ways.

For instance, in order to mitigate the effects of over-fitting, in some implementations, the RBF model can be regularized according to a cost function that penalizes oscillatory behavior. The measurement data with noise can be described by:

$$F(\vec{x}_i) = \vec{y}_i + \varepsilon_i, i = 1, 2, \ldots, N,$$

where $$F(\vec{x}) = \sum_{i=1}^{N} \vec{w}_i \varphi(\|\vec{x} - \vec{x}_i\|),$$

assuming the centers of the RBF functions are the set of training inputs, and $\varepsilon_i$ is the noise in the measurement data. The RBF model can be obtained by minimizing the following cost function:

$$E(F) = \sum_{i=1}^{N} (F(\vec{x}_i) - \vec{y}_i)^2 + \lambda \sum_{i=1}^{N} \vec{w}_i^2,$$

where $$\sum_{i=1}^{N} (F(\vec{x}_i) - \vec{y}_i)^2$$

is the fitting error, and $$\sum_{i=1}^{N} \vec{w}_i^2$$

is the regularization term to penalize the oscillations in the fitting. The parameter controls the balance between fitting the data and avoiding the penalty, and can be assigned different values depending on the desired fitting behavior. In some implementations, the value of parameter can be determined using generalized cross-validation methods in order to assess the accuracy of the resulting RBF model. Example cross-validation methods include K-fold cross validation, repeated random sub-sampling validation, and leave-one-out cross-validation.

Figure 8:
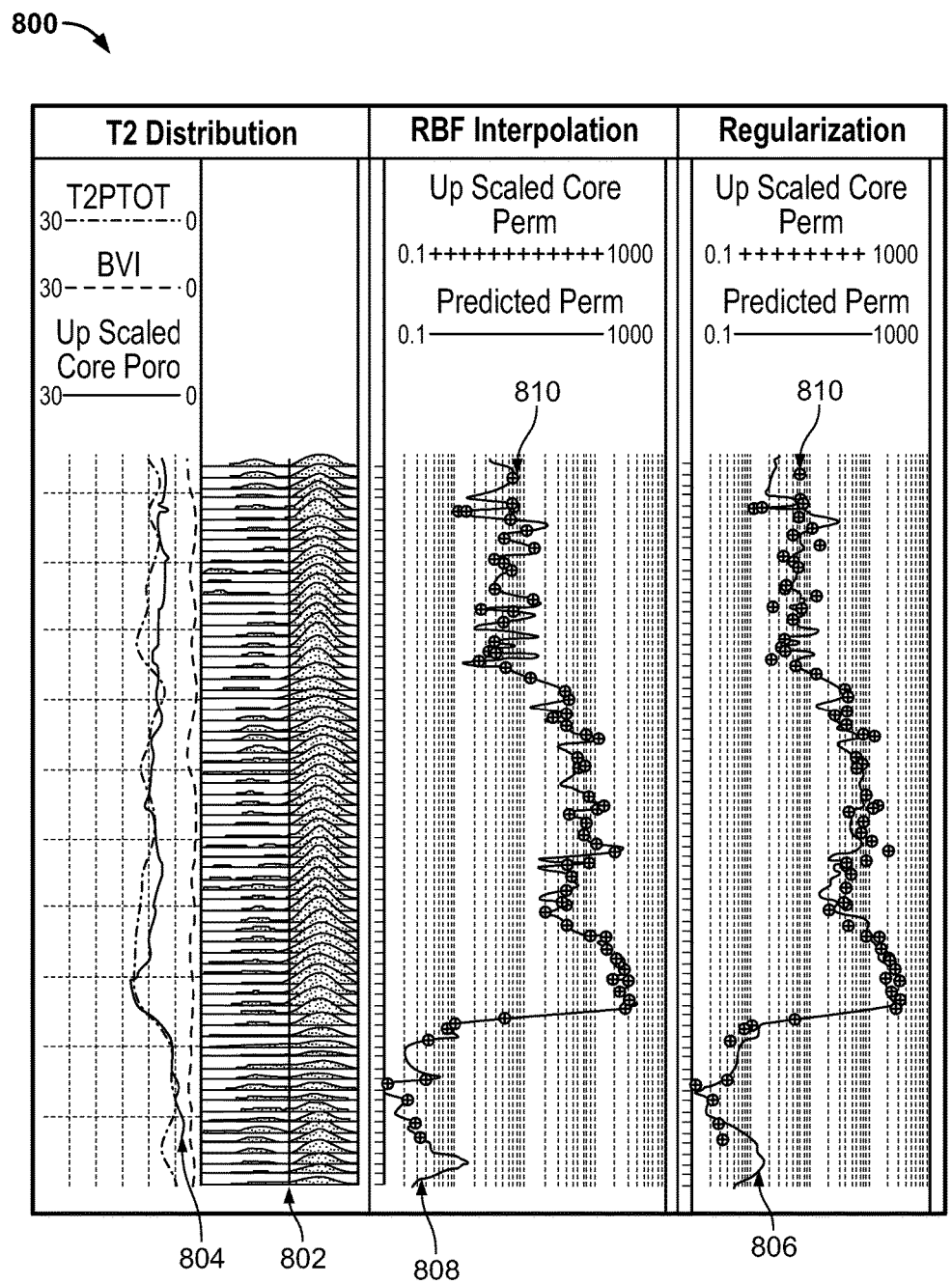
FIG. 8 includes plots of the permeability predictions of an example RBF model and the permeability predictions of another example RBF model that has been regularized.

FIG. 8 shows a plot 800 that compares the permeability predictions of the RBF model with and without regularization. Based on an example training database of relaxation-time distributions 802 and measured permeability values 804, the resulting regularized RBF model (line 806) exhibits a lesser degree of over-fitting compared to that of a non-regularized RBF model (line 808), and is less likely to be over-fit to the plotted measured permeability values (crosses 810). As a result, the regularized RBF model 806 is smoother, and is less susceptible to noise in the training database.

In some implementations, in order to mitigate the effects of over-fitting, the centers of RBF model can be derived from only a subset of the relaxation-time distributions of the training database. That is, instead of using all the data of the training database for the centers of the RBF model, only a subset of the data set is selected for the centers of the RBF model. For example, in some implementations, the goal of this selection is to find a subset which can explain most, but not all, of the variation in the training set, with the goal of avoiding over-fitting noise. In some instances, a subset of the training samples are used for the centers of the RBF model, and all the training samples (including the subset) are used to compute other parameters (e.g., the weights) of the RBF model.

An optimal or otherwise acceptable subset of training data used for the centers of the RBF model can be selected using various techniques. For instance, in the forward selection technique, individual centers can be added to the model one at a time, and each center can be tested for inclusion in the model. The most significant of these centers can then be added to the model.

An example implementation of forward selection can be performed, where C is the collection of the centers of the RBF model, C1 is the collection of data which are candidates of the centers of the RBF model, and where initially C is empty and C1 is the training database. For each sample center in the collection C1, an RBF model can be constructed whose centers are the selected samples from C1 and the samples in the collection C. A sample center with the smallest SEE (i.e., is the sum of squared errors over all the sample centers in the training data set) is removed from C1 and added into C. This can be repeated, for example, until C1 is empty, or certain stop criteria is met.

There are several criteria which can be used to stop the selection process. For instance, the number of selected centers can be selected in order to minimize criteria such as the Bayesian information criterion (BIC), or the generalized cross-validation (CGV) criterion. For example, in a non-regularized RBF model, a CGV criterion can be represented as $$GCV = \frac{N}{(N-M)^2} SSE,$$

where N is the number of sample centers in the training database and M is the number of centers in the RBF model. In another example, in a non-regularized RBF model, a BIC can be represented as $$BIC = \frac{N + (\ln(N) - 1)M}{N(N-M)} SSE.$$

Figure 9:
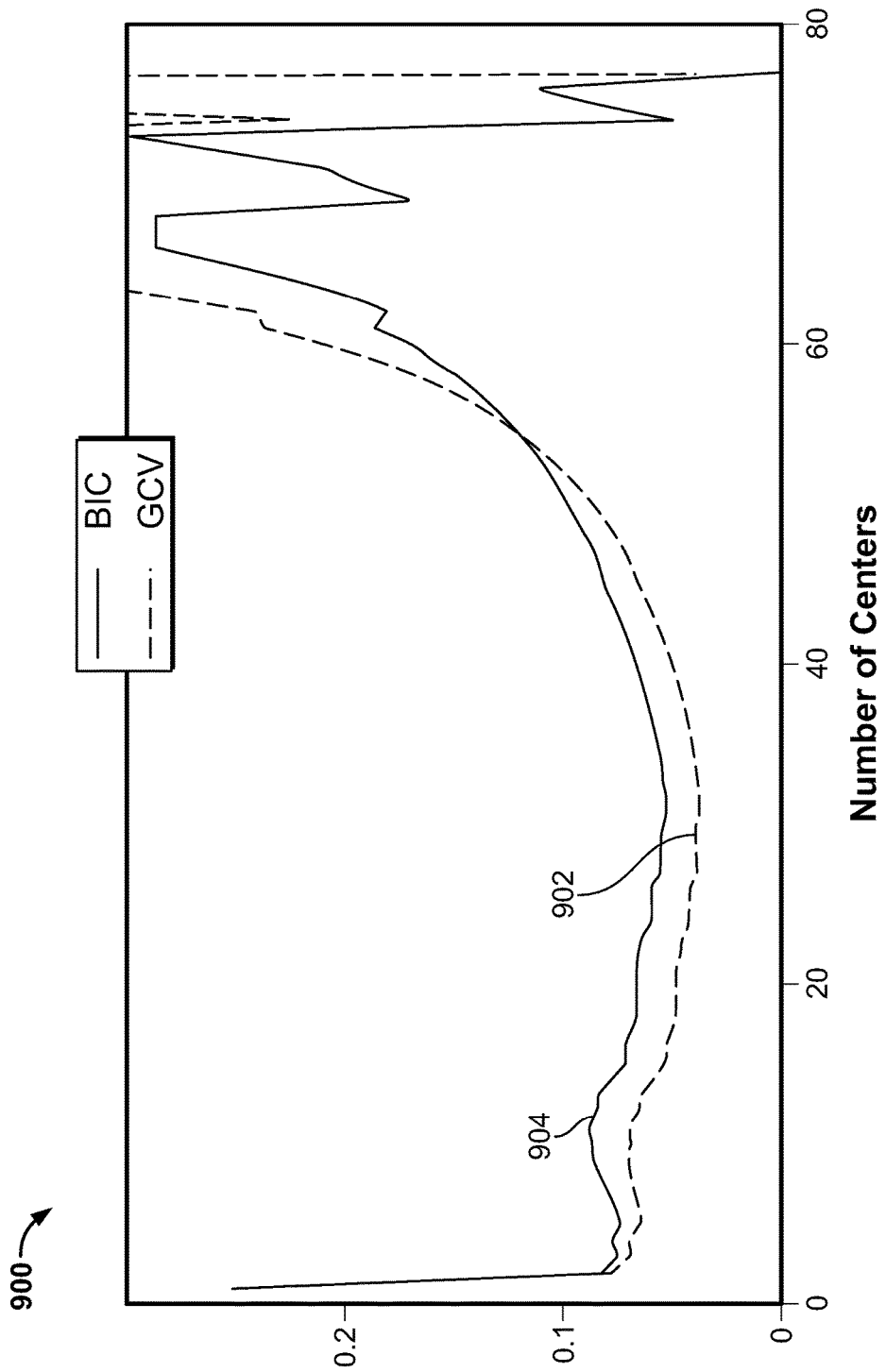
FIG. 9 is a plot that shows the relationship between stop criteria and the number of selected centers.

Referring to FIG. 9, when GCV and BIC are plotted for an example training database (as shown in plot 900), GCV 902 and BIC 904 are minimized when the number of selected centers is 31. Thus, in the case of this example training database, 31 centers can be selected.

Figure 10:
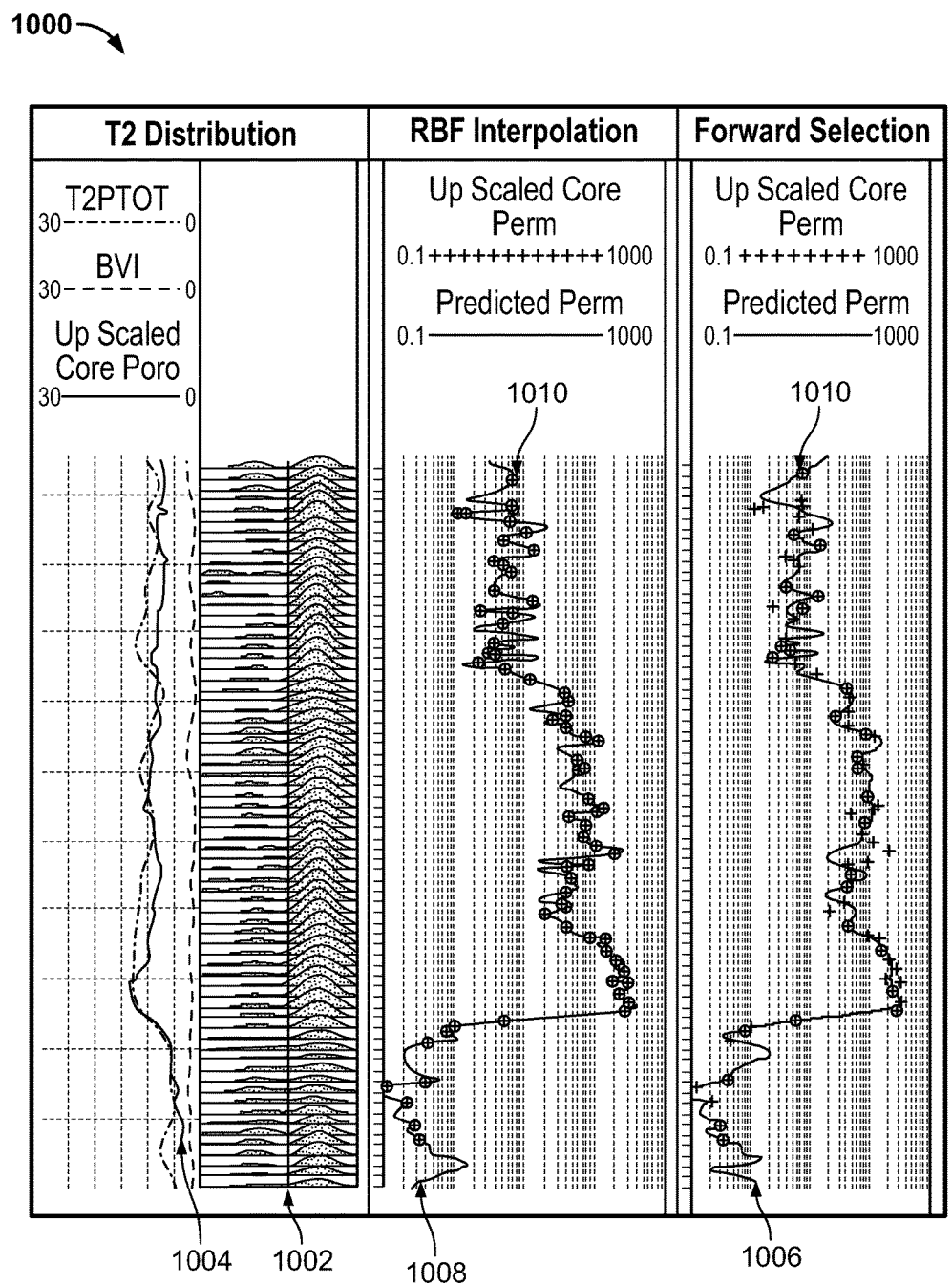
FIG. 10 includes plots of permeability predictions of an example RBF model and permeability predictions of another example RBF model that was trained using forward selection.

FIG. 10 shows a plot 1000 that compares the permeability predictions of the RBF model with and without forward selection. Based on an example training database of relaxation-time distributions 1002 and measured permeability values 1004, the RBF model determined through forward selection (line 1006) exhibits a lesser degree of over-fit compared to that of the RBF interpolation model (line 1008), and is less likely to be over-fit to the plotted measured permeability values (crosses 1010). As a result, the RBF model 1006 determined through forward selection is smoother, and is less susceptible to noise in the training database.

In some implementations, backward selection can be used instead of forward selection. In an example implementation, for an RBF model whose centers are made of all the samples in the training database, individual centers can be removed from the model one at a time, and each center can be tested for subtraction from the model.

Figure 11:
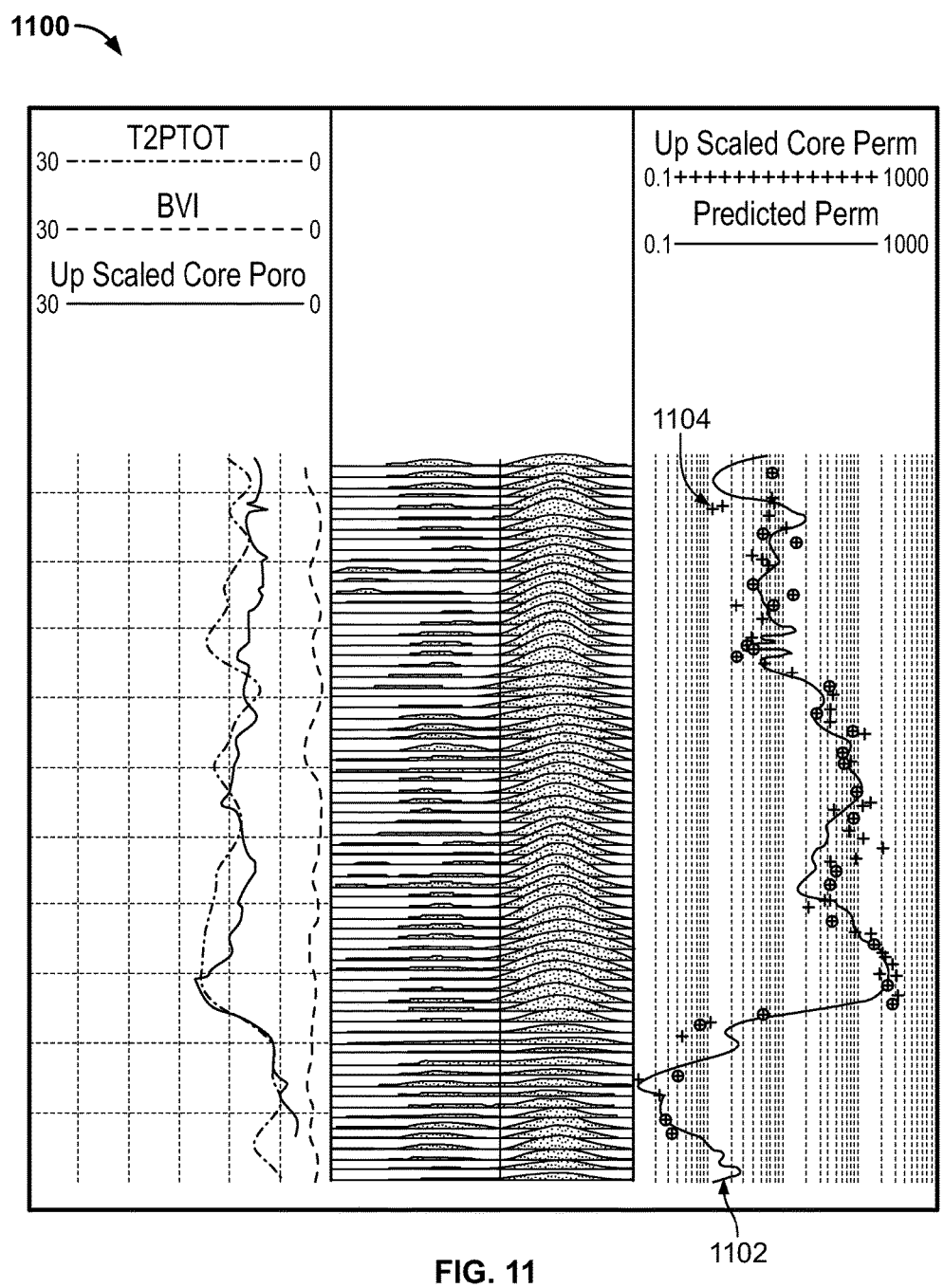
FIG. 11 includes plots of permeability predictions based on an example RBF model in which the RBF model is regularized after centers are selected using forward selection.

Multiple techniques can be simultaneously used to reduce over-fitting. For example, in some implementations, regularization is applied at each step of the forward selection method. In another example, in order to reduce computation requirements, regularization is applied to the RBF model after centers are selected using forward selection. FIG. 11 shows a plot 1100 that shows the permeability predictions based on an RBF model (line 1102) in which the RBF model is regularized after centers are selected using forward selection. The resulting RBF model (line 1102) is smoother than that obtained from either forward selection or regularization alone (for example, compared to the RBF models represented by line 806 in FIG. 8 and line 1006 in FIG. 10), and is less likely to be over-fit to the plotted measured permeability values (crosses 1104). Thus, the RBF model is even less susceptible to noise in the training database.

In some implementations, the spatial resolution of the core permeability measurements differs from the spatial resolution of the NMR measurements. Generally, the NMR measurements can have higher, lower or the same resolution as the core permeability measurements. In some implementations, the core permeability measurements have a relatively higher vertical resolution, while the NMR measurements have a relatively lower vertical resolution. In some implementations, the vertical resolution of NMR measurements is limited to the length of the NMR tool antenna. In an example, the antenna of a MRIL Prime tool can be about 33 inches, while the core permeability measures can be obtained from core plugs approximately 1 to 2 inches in length. During modeling training, the core permeability measurements can be scaled to match the resolution of the NMR measurements.

Various techniques can be used to upscale the core measurements. In an example, a geometric average technique can be used to upscale the core permeability measurements. The degree of upscale can be determined by matching the NMR measurements with up-scaled core porosity measurements. The core porosity measurements can be up-scaled by the arithmetic mean weighted with the thickness of each core sample (since porosity is a volumetric-based parameter). The variance in the scaled core porosities can be similar to that in the NMR porosities.

Figure 12A:
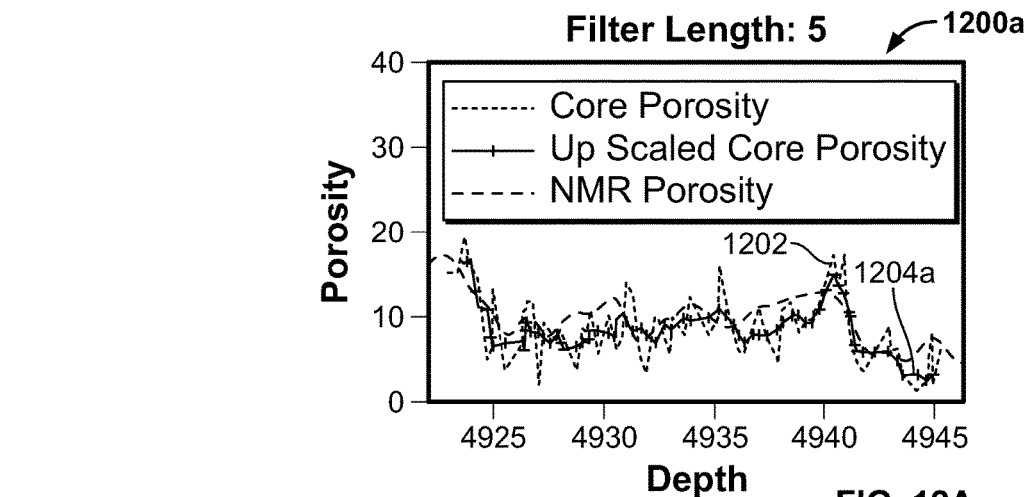
FIGS. 12A-C include plots showing porosity measurements obtained using routine core analysis (RCA) that have been up-scaled by varying filter lengths.
Figure 12B:
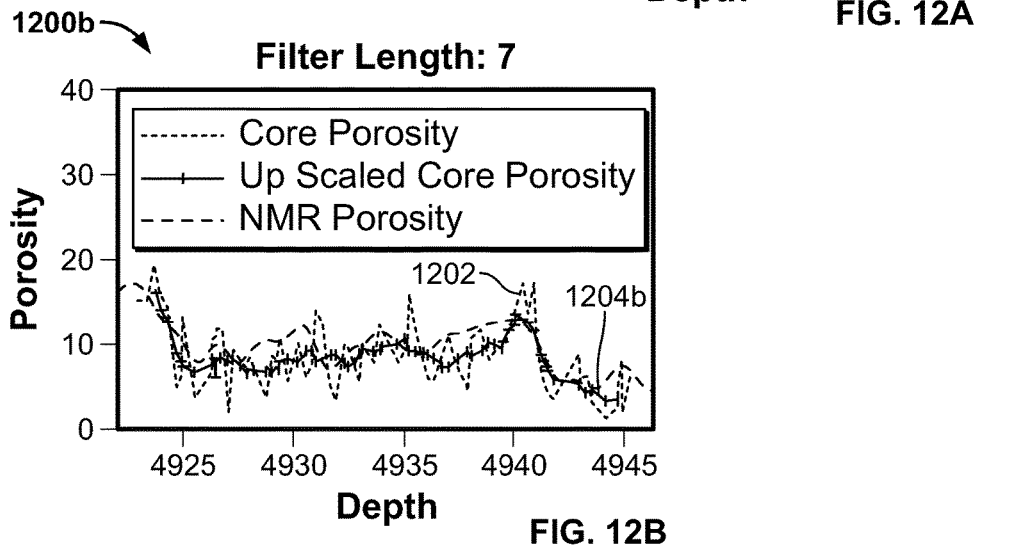
Figure 12C:
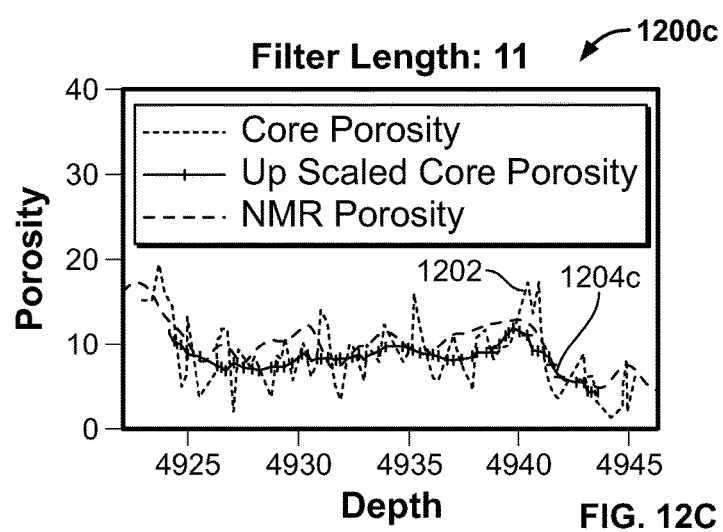
Figure 13:
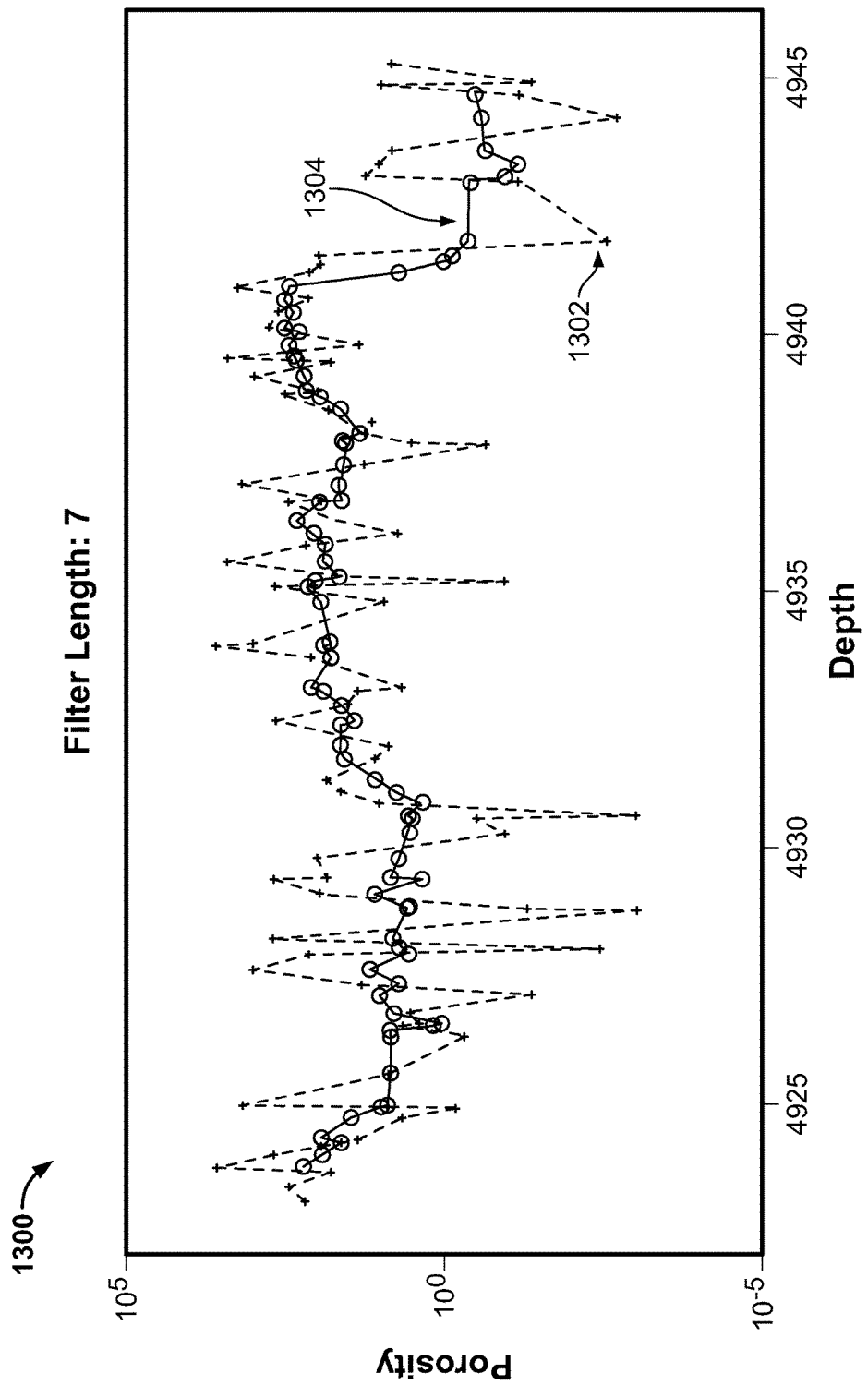
FIG. 13 is a plot comparing core porosity measurements before and after they have been up-scaled by a filter.

FIGS. 12A-C show plots 1200a-c of core porosity measurements that have been up-scaled by varying filter lengths (i.e., the number of samples used to compute the average.) For example, plot 1200a shows the core porosity measurements 1202 that have been up-scaled to measurements 1204a by a filter length of 5, plot 1200b shows the same core porosity measurements 1202 that have been up-scaled to measurements 1204b by a filter length of 7, and plot 1200c shows the same core porosity measurements 1202 that have been up-scaled to measurements 1204c by a filter length of 11. In some implementations, the filter length used can be selected empirically. For instance, FIG. 13 shows a plot 1300 for an example training database in which a filter length of 7 is used to convert the original core permeability measurements (solid circles 1302) to up-scaled permeability measurements (outlined circles 1304).

Figure 14:
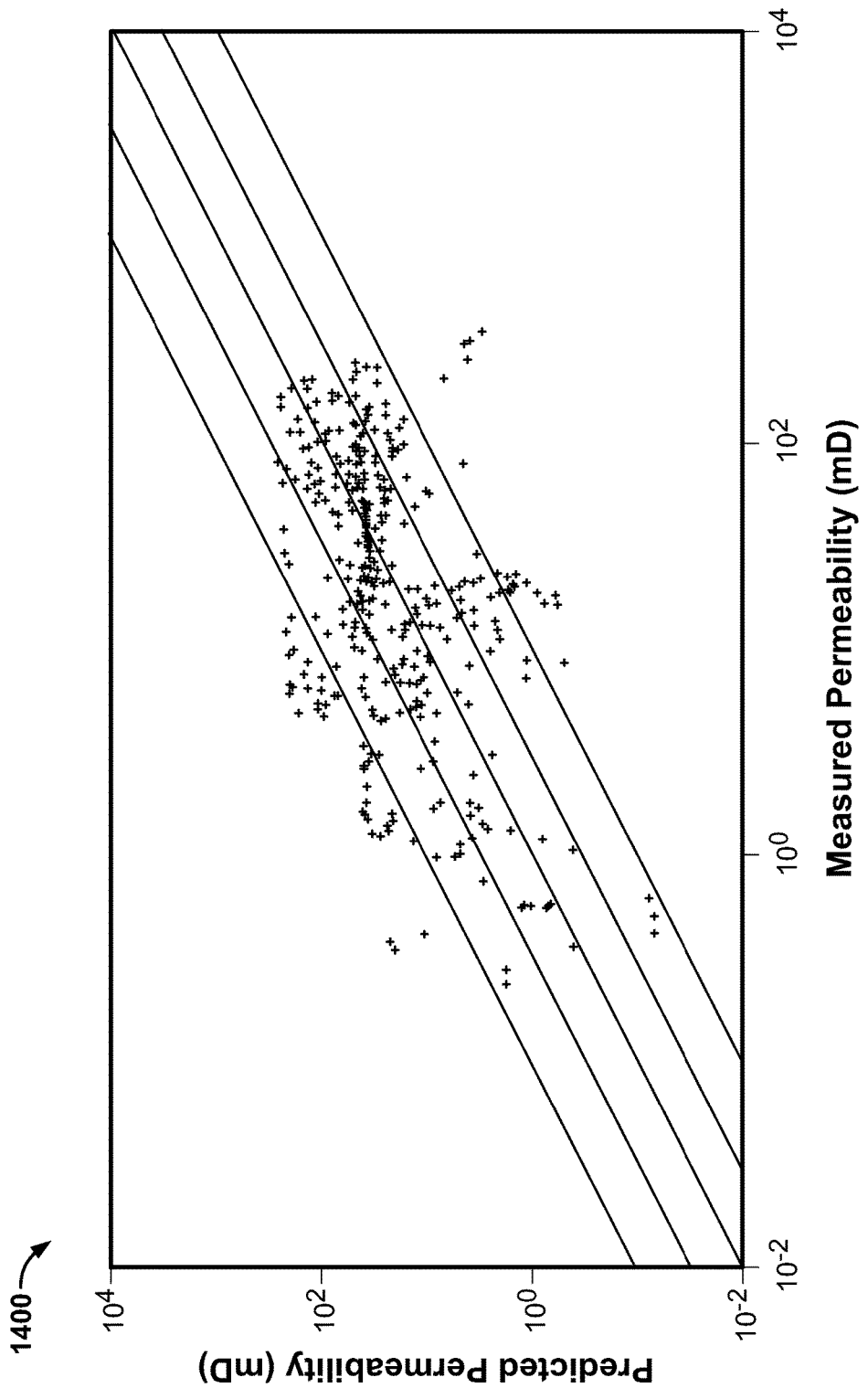
FIG. 14 is a plot that compares measured permeability and permeability predicted by an example RBF model trained using measurement data from another well.

In some implementations, an RBF model developed using training data from one well can be used to predict permeability from NMR measurements of another well, with the accuracy of the prediction depending on the data of the training database and whether the two wells have similar characteristics. To test the accuracy of the RBF model, two RBF models can be developed for each well, each with its own core permeability measurement data and NMR relaxation-time distributions. Referring to FIG. 14, plot 1400 shows the accuracy of an example RBF model tested with the "leave one out" method. However, in some implementations, the "leave one out" method does not reveal whether the RBF model exhibits over-fitting, and in some circumstances, can lead to poor generalization performance. As an alternative, in some implementations, the RBF model can be validated by dividing the data of the training database into two sets: one set for use in RBF model development, and another set for validation. However, in some circumstances, this practice may introduce bias, as the RBF model performance depends on the subset selection.

Figure 15:
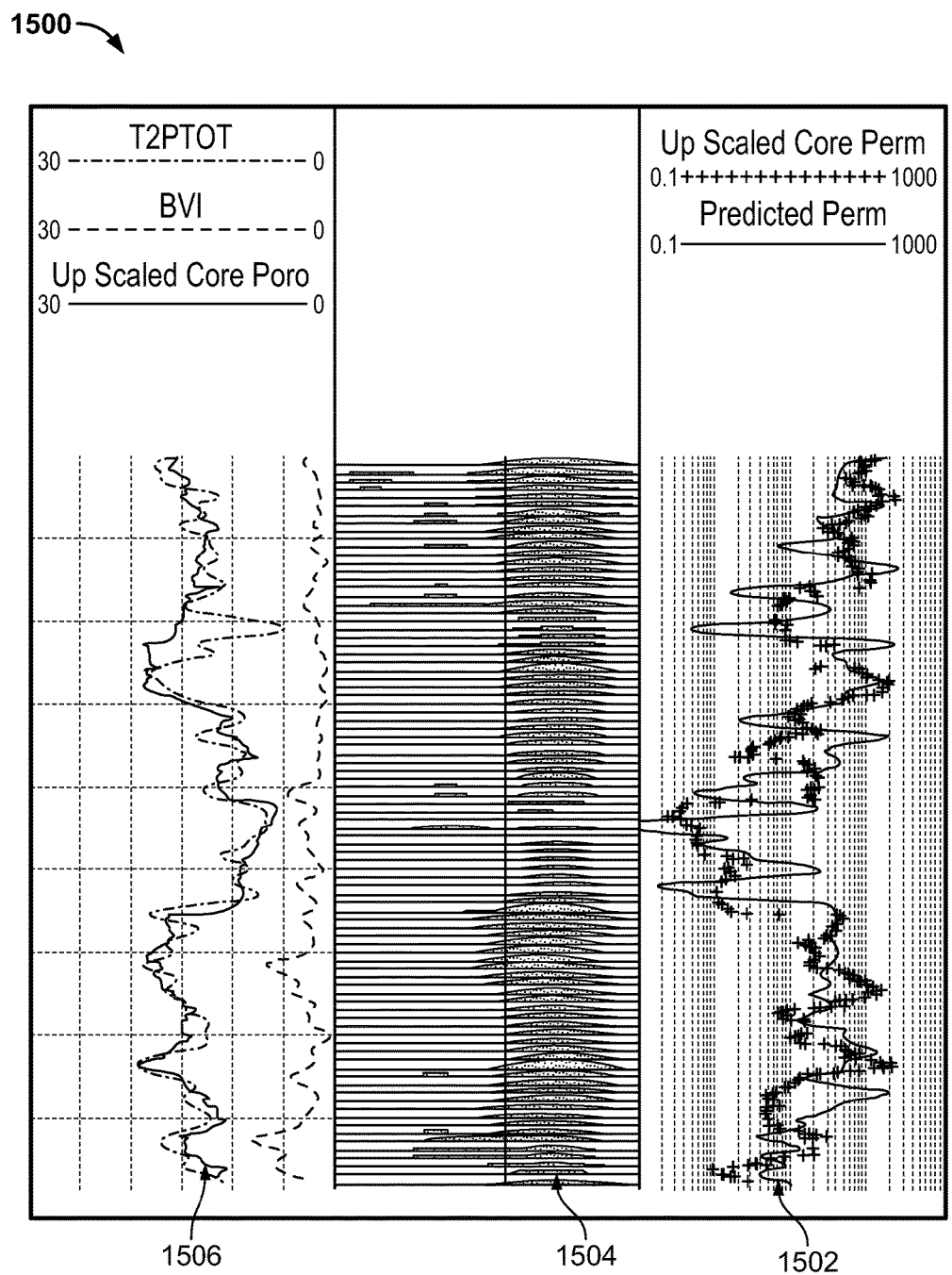
FIG. 15 shows the permeability predictions for a first well using an RBF model trained using measurement data obtained from another well.

As an alternative to these techniques, in some implementations, the RBF model can be validated by predicting the permeability for one well with the training data set from another well. FIG. 15 shows a plot 1500 that illustrates the permeability predictions 1506 for a first well, based on relaxation-time distribution 1504 acquired from the first well and an RBF model 1502 trained using measurement data, including relaxation-time distributions and core permeability measurements obtained from another well.

Some embodiments of subject matter and operations described in this specification can be implemented in digital electronic circuitry, or in computer software, firmware, or hardware, including the structures disclosed in this specification and their structural equivalents, or in combinations of one or more of them. Some embodiments of subject matter described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 16:
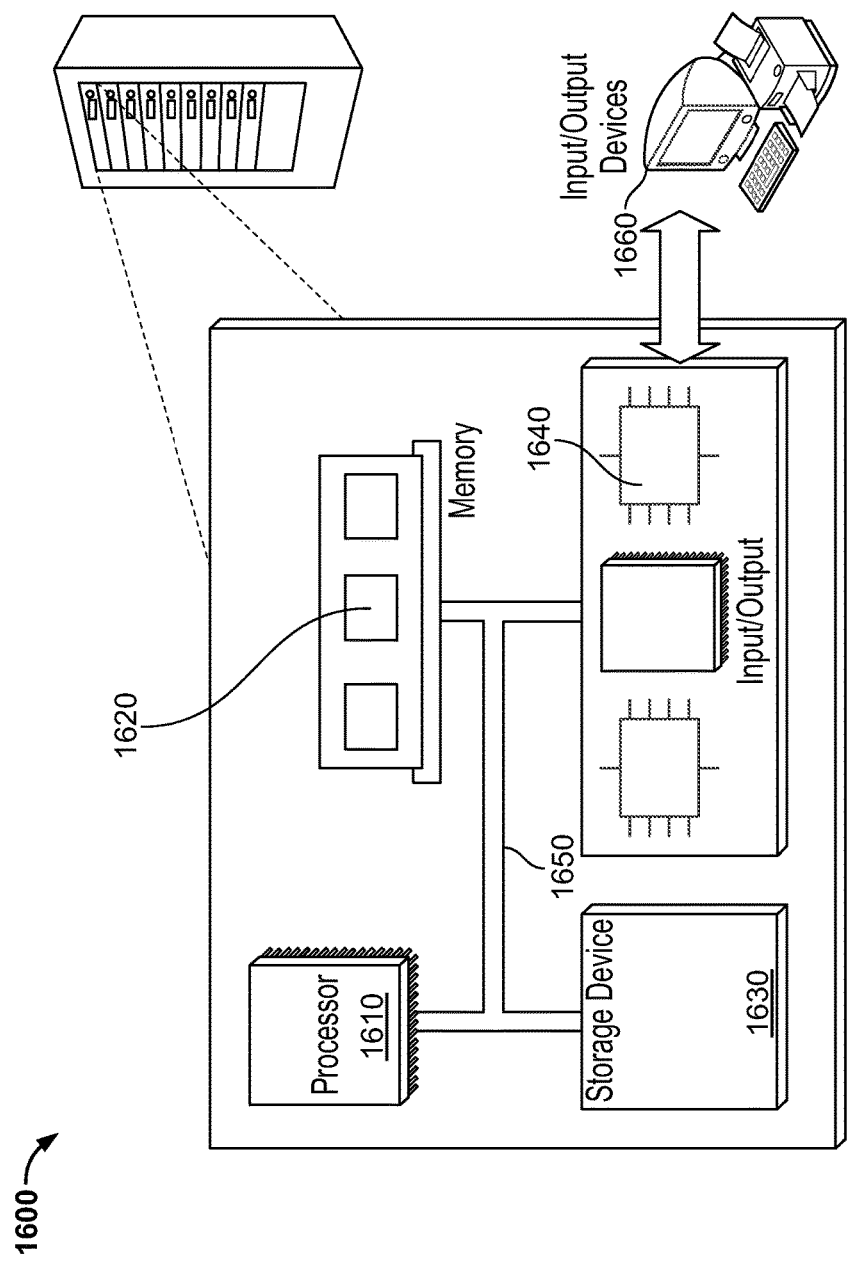
FIG. 16 shows a diagram of an example computer system.

FIG. 16 shows an example computer system 1600. The system 1600 includes a processor 1610, a memory 1620, a storage device 1630, and an input/output device 1640. Each of the components 1610, 1620, 1630, and 1640 can be interconnected, for example, using a system bus 1650. The processor 1610 is capable of processing instructions for execution within the system 1600. In some implementations, the processor 1610 is a single-threaded processor, a multi-threaded processor, or another type of processor. The processor 1610 is capable of processing instructions stored in the memory 1620 or on the storage device 1630. The memory 1620 and the storage device 1630 can store information within the system 1600.

The input/output device 1640 provides input/output operations for the system 1600. In some implementations, the input/output device 1640 can include one or more network interface devices, e.g., an Ethernet card; a serial communication device, e.g., an RS-232 port; and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 1660. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of examples have been described. Nevertheless, it will be understood that various modifications can be made. Accordingly, other implementations are within the scope of the following claims.

The invention claimed is:

1. A method of training a subterranean formation permeability model based on nuclear magnetic resonance (NMR) data, the method comprising:
    acquiring NMR measurements associated with at least one subterranean region using a downhole NMR logging tool;
    accessing a plurality of relaxation-time distributions generated from the NMR measurements;
    normalizing the plurality of relaxation-time distributions;
    generating multiple sets of principal components from the normalized relaxation-time distributions by applying a principle component analysis to the normalized relaxation-time distributions, each set of principal components representing a respective one of the normalized relaxation-time distributions;
    computing parameters for a plurality of weighted radial basis functions based on the sets of principal components and measured permeability values of the at least one subterranean region; and
    producing a subterranean formation permeability model that includes the weighted radial basis functions and the computed parameters.

2. The method of claim 1, wherein said normalizing includes normalizing each relaxation-time distribution to a common normalizing value.

3. The method of claim 1, wherein said generating multiple sets of principal components comprises:
    defining a training dataset matrix that includes the plurality of relaxation-time distributions;
    computing a covariance matrix from the training dataset matrix;
    defining a transformation matrix from k eigenvectors that correspond to k largest eigenvalues of the covariance matrix, where k is a positive integer;
    generating a transformed dataset matrix by applying the transformation matrix to the training dataset matrix; and
    extracting the sets of principal components from the training dataset matrix, where each set of principal components includes first k principal components representing the respective one of the relaxation-time distributions.

4. The method of claim 3, comprising selecting k based on a level of noise in the relaxation-time distributions.

5. The method of claim 1, comprising selecting a subset of the relaxation-time distributions that meet a Bayesian information criterion or a generalized cross-validation criterion to be centers of the respective radial basis functions using a forward selection.

6. The method of claim 1, wherein said computing the parameters includes using a cost function to reduce a magnitude of variation among weighting parameters of the weighted radial basis functions.

7. The method of claim 1, comprising:
    accessing permeability and porosity measurements obtained from core samples extracted from the at least one subterranean region; and
    computing the parameters based on the sets of principal components, and the permeability and porosity measurements.

8. The method of claim 1, further comprising:
    generating an input set of principal components from an input relaxation-time distribution obtained independently from the NMR measurements; and
    determining a permeability of a subterranean region associated with the input set of principal components using the subterranean formation permeability model that takes the input set of principal components as an input to the weighted radial basis functions.

9. A system comprising:
    a downhole NMR logging tool adapted to acquire NMR measurements of at least one subterranean region;

a computing system comprising:
a communication interface operable to receive the NMR measurements; and
a data processing apparatus operable to perform operations that include:
generating a plurality of relaxation-time distributions from the NMR measurements;
normalizing the plurality of relaxation-time distributions;
generating multiple sets of principal components from the normalized relaxation-time distributions by applying a principle component analysis to the normalized relaxation-time distributions, each set of principal components representing a respective one of the relaxation-time distributions;
computing parameters for a plurality of weighted radial basis functions based on the sets of principal components and measured permeability values of the at least one subterranean region; and
producing a subterranean formation permeability model that includes the weighted radial basis functions and the computed parameters.

10. The system of claim 9, wherein the downhole NMR logging tool acquires the NMR measurements in situ.

11. The system of claim 9, further comprising a laboratory NMR system that acquires the NMR measurements ex situ.

12. The system of claim 9, wherein said normalizing includes normalizing each relaxation-time distribution to a common normalizing value.

13. The system of claim 9, wherein said generating multiple sets of principal components comprises:
defining a training dataset matrix that includes the plurality of relaxation-time distributions;
computing a covariance matrix from the training dataset matrix;
defining a transformation matrix from k eigenvectors that correspond to k largest eigenvalues of the covariance matrix, where k is a positive integer;
generating a transformed dataset matrix by applying the transformation matrix to the training dataset matrix; and
extracting the sets of principal components from the training dataset matrix, where each set of principal components includes first k principal components representing the respective one of the relaxation-time distributions.

14. The system of claim 13, wherein the operations further comprise selecting k based on a level of noise in the relaxation-time distributions.

15. The system of claim 9, wherein the operations further comprise selecting a subset of the relaxation-time distributions to be centers of the respective radial basis functions.

16. The system of claim 9, wherein said computing the parameters includes using a cost function to reduce a magnitude of variation among weighting parameters of the weighted radial basis functions.

17. The system of claim 9, wherein the operations further comprise:
accessing permeability and porosity measurements obtained from a core sample extracted from the at least one subterranean region; and
computing the parameters based on the sets of principal components, and the permeability and porosity measurements.

18. A non-transitory computer readable medium storing instructions that are operable when executed by a data processing apparatus to perform operations comprising:
acquiring NMR measurements associated with at least one subterranean region using a downhole NMR logging tool;
accessing a plurality of relaxation-time distributions generated from the NMR measurements;
normalizing the plurality of relaxation-time distributions;
generating multiple sets of principal components from the normalized relaxation-time distributions by applying a principle component analysis to the normalized relaxation-time distributions, each set of principal components representing a respective one of the normalized relaxation-time distributions;
computing parameters for a plurality of weighted radial basis functions based on the sets of principal components and measured permeability values of the at least one subterranean region; and
producing a subterranean formation permeability model that includes the weighted radial basis functions and the computed parameters.

19. The computer readable medium of claim 18, wherein said normalizing includes normalizing each relaxation-time distribution to a common normalizing value.

20. The computer readable medium of claim 18, wherein said generating multiple sets of principal components comprises:
defining a training dataset matrix that includes the plurality of relaxation-time distributions;
computing a covariance matrix from the training dataset matrix;
defining a transformation matrix from k eigenvectors that correspond to k largest eigenvalues of the covariance matrix, where k is a positive integer;
generating a transformed dataset matrix by applying the transformation matrix to the training dataset matrix; and
extracting the sets of principal components from the training dataset matrix, where each set of principal components includes first k principal components representing the respective one of the relaxation-time distributions.

21. The computer readable medium of claim 20, the operations further comprising selecting k based on a level of noise in the relaxation-time distributions.

22. The computer readable medium of claim 18, the operations further comprising selecting a subset of the relaxation-time distributions to be centers of the respective radial basis functions.

23. The computer readable medium of claim 18, wherein said computing the parameters includes using a cost function to reduce a magnitude of variation among weighting parameters of the weighted radial basis functions.

24. The computer readable medium of claim 18, the operations further comprising:
accessing permeability and porosity measurements obtained from core samples extracted from the at least one subterranean region; and
computing the parameters based on the sets of principal components, and the permeability and porosity measurements.

25. The computer readable medium of claim 18, the plurality of relaxation-time distributions comprising a first plurality of relaxation-time distributions generated from a first subterranean region, the operations further comprising:
accessing a second plurality of relaxation-time distributions generated from NMR logging data acquired from a second subterranean region; and computing a permeability of the second subterranean region using the permeability model and the second plurality of relaxation-time distributions.

* * * * *

UNITED STATES PATENT AND TRADEMARK OFFICE
CERTIFICATE OF CORRECTION

PATENT NO. : 10,197,697 B2
APPLICATION NO. : 14/397835
DATED : February 5, 2019
INVENTOR(S) : Wei Shao and Songhua Chen Page 1 of 1

It is certified that error appears in the above-identified patent and that said Letters Patent is hereby corrected as shown below:

In the Specification

Column 4, Line 29, after --including the-- delete "Can" and insert --Carr--

Column 6, Lines 31-32, delete " $\sum_{i=k}^{N} \phi_i$ " and insert -- $\sum_{i=1}^{N} \phi_i$ --

Column 12, Line 59, delete "parameter controls" and insert --parameter $\lambda$ controls--

Column 12, Line 62, after --value of-- delete "parameter" and insert --parameter $\lambda$--

Signed and Sealed this
Twenty-third Day of July, 2019

Andrei Iancu
*Director of the United States Patent and Trademark Office*